United States Patent [19]
Munroe et al.

[11] Patent Number: 6,057,126
[45] Date of Patent: *May 2, 2000

[54] MAMMALIAN EDG-5 RECEPTOR HOMOLOGS

[75] Inventors: Donald G. Munroe, Waterdown; Ashwani K. Gupta; Tejal B. Vyas, both of Mississauga, all of Canada; Jerold J. M. Chun, LaJolla, Calif.

[73] Assignee: Allelix Biopharmaceuticals, Inc., Ontario, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/997,803

[22] Filed: Dec. 24, 1997

[51] Int. Cl.$^7$ .......................... C12N 15/12; C12N 15/85; C07H 21/04

[52] U.S. Cl. ..................... 435/69.1; 435/320.1; 435/325; 435/440; 435/455; 536/23.1; 536/23.5; 536/24.31; 536/24.33

[58] Field of Search .................................... 435/69.1, 440, 435/320.1, 455, 91.1; 536/23.1, 23.5, 24.31, 24.33

[56] References Cited

FOREIGN PATENT DOCUMENTS 0 878 479 A   11/1998   European Pat. Off. .

OTHER PUBLICATIONS

Burnstock G.: "P2 purinoreceptors: historical perspective and classification"Ciba Foundation Symposium, vol. 198, 1996, pp. 1–34.

An S. et al.: "identification of cDNAs encoding two G protein–coupled receptors for lysosphingolipids"Febs Letters, vol. 417, no. 3, Dec. 17, 1997, pp. 279–282.

Lee et al.: "Molecular biology of G–protein–coupled receptors"Drug News and Perspectives, vol. 6, no. 7, Sep. 1. 1993, pp. 488–497.

An et al.: "Molecular Cloning of the Human Edg2 Protein and Its Identification as a Functional Cellular Receptor for Lysophosphatidic Acid", Biochemical and Biophysical Research Communications vol. 231. no. 3, Feb. 24, 1997, pp. 617–622.

Oliveira et al.: "A Common motif in G–protein coupled seven transmembrane helix receptors"Journal of Computer–Aided Molecular Design, vol. 7, no. 6, Dec. 1, 1993, pp. 649–658.

Primary Examiner—John L. LeGuyader
Assistant Examiner—Mark L. Shibuya
Attorney, Agent, or Firm—Nikaido, Marmelstein, Murray & Oram LLP

[57] ABSTRACT

The present invention describes a nucleic acid sequence and an amino acid sequence for novel mammalian, including human, EDG-5 receptor homologs.

8 Claims, 9 Drawing Sheets

Fig. 1

```
1   AACACTGGCC CGGTGTCGAA AACGTTGACC GTCAACCGCT GGTTCCTCCG

51  CCAGGGGCTC CTAGACACCA GCCTGACTGC CTCCCTGGCC AATTTGCTGG

101 TTATTGCTGT GGAAAGACAC ATGTCNATCA TGAGGATGAG AGTCCACAGC

151 AACTTGACCA AAAAGCGGGT GACGCTGCTC ATTCTGCTGG TGTGGGCCAT

201 CGCCATCTTC ATGGGGGCCG TCCCCACNCT GGGATGGAAT TGCCTCTGCA

251 ACATCTCGGC CTGCTCTTCT CTGGCTCCCA TTTACAGTAG GAGTTACCTC

301 ATTTTCTGGA CTGTGTCCAA CCTCCTGGCC TTCTTCATCA TGGTGGCGGT

351 ATACGTACGC ATCTACATGT ATGTTAAAAG GAAAACCAAC GTCTTATCTC

401 CACACACCAG TGGCTCCATC AGCCGCCGGA GGGCTCCCAT GAAGCTAATG

451 AAGACAGTGA TGACCGTCTT AGGCGCCTTC GTGGTGTGCT GGACCCCGGG

501 TCTGGTGGTT CTGCTGCTGG ACGGCCTGAA CTGCAAGCAG TGTAACGTGC

551 AACACGTGAA GNGCTGGTTC CTGCTGCTCG CACTGCTCAA CTCCGTCATG

601 AACCCCCTCA TCTACTGCCG CTCTCCNNAC TTTCCATGG
```

Fig. 2

```
  1  NTGPVSKTLT VNRWFLRQGL LDTSLTASLA NLLVIAVERH MSIMRMRVHS

51  NLTKKRVTLL ILLVWAIAIF MGAVPTLGWN CLCNISACSS LAPIYSRSYL

101  IFWTVSNLLA FFIMVAVYVR IYMYVKRKTN VLSPHTSGSI SRRRAPMKLM

151  KTVMTVLGAF VVCWTPGLVV LLLDGLNCKQ CNVQHVKXWF LLLALLNSVM

201  NPLIYCRSPX FPW
```

Fig. 3

```
   1  gaattcgcgg ccgcgtcgac gttcaCTTCT CCACAATGAA TGAGTGTCAC
  51  TATGACAAGC ACATGGACTT TTTTTATAAT AGGAGCAACA CTGATACTGT
 101  CGATGACTGG ACAGGAACAA AGCTTGTGAT TGTTTTGTGT GTTGGGACGT
 151  TTTTCTGCCT GTTTATTTTT TTTTCTAATT CTCTGGTCAT CGCGGCAGTG
 201  ATCAAAAACA GAAAATTTCA TTTCCCCTTT TACTACCTGT TGGCTAATTT
 251  AGCTGCTGCC GATTTCTTCG CTGGAATTGC CTATGTATTC CTGATGTTTA
 301  ACACAGGCCC AGTTTCAAAA ACTTTGACTG TCAACCGCTG GTTTCTCCGT
 351  CAGGGGCTTC TGGACAGTAG CTTGACTGCT TCCCTCACCA ACTTGCTGGT
 401  TATCGCCGTG GAGAGGCACA TGTCAATCAT GAGGATGCGG GTCCATAGCA
 451  ACCTGACCAA AAAGAGGGTG ACACTGCTCA TTTTGCTTGT CTGGGCCATC
 501  GCCATTTTTA TGGGGGCGGT CCCCACACTG GCTGGAATT GCCTCTGCAA
 551  CATCTCTGCC TGCTCTTCCC TGGCCCCCAT TTACAGCAGG AGTTACCTTG
 601  TTTTCTGGAC AGTGTCCAAC CTCATGGCCT TCCTCATCAT GGTTGTGGTG
 651  TACCTGCGGA TCTACGTGTA CGTCAAGAGG AAAACCAACG TCTTGTCTCC
 701  GCATACAAGT GGGTCCATCA GCCGCCGGAG GACACCCATG AAGCTAATGA
 751  AGACGGTGAT GACTGTCTTA GGGGCGTTTG TGGTATGCTG GACCCCGGGC
 801  CTGGTGGTTC TGCCCCTCGA CGGCCTGAAC TGCAGGCAGT GTGGCGTGCA
 851  GCATGTGAAA AGGTGGTTCC TGCTGCTGGC GCTGCTCAAC TCCGTCGTGA
 901  ACCCCATCAT CTACTCCTAC AAGGACGAGG ACATGTATGG CACCATGAAG
 951  AAGATGATCT GCTGCTTCTC TCAGGAGAAC CCAGAGAGGC GTCCCTCTCG
1001  CATCCCCTCC ACAGTCCTCA GCAGGAGTGA CACAGGCAGC CAGTACATAG
1051  AGGATAGTAT TAGCCAAGGT GCAGTCTGCA ATAAAAGCAC TTCCTAAACT
1101  CTGGATGCCT CTYGGCCCAC CCAGGCCTCC TCTGGGAAAA GAGCTGTTAA
1151  GAATGATTAC CTGTCTCTAA CAAAGCCCAT GTACAGTGTT ATTTGAGGTC
1201  TCCATTAATC ACTGCTAGAT TTCTTTAAAA AATTTTTTTT CATAGTTTAA
1251  AAGCATGGGC AGTAAAGAGA GGACCTGCTG CATTTAGAGA AAGCACAGgt
1301  cgacgcggcc gcgaattctt ttgcttttta ccctggaaga aatactcgag
1351  catgcat
```

Fig. 4A

```
    caccttcctaacctgagcggcctagcctgggaaacaaacaattaaaatgtgcgctaaatg
  1 ------------+---------+---------+---------+---------+---------+  60
    gtggaaggattggactcgccggatcggacccttttgtttgttaattttacacgcgatttac ctgtggtaggaggtcaggggctatgtcctggaccaaaggacatttgcactgagacctgac
 61 ------------+---------+---------+---------+---------+---------+ 120
    gacaccatcctccagtccccgatacaggacctggtttcctgtaaacgtgactctggactg acttcaggtcttcaactcccttgatgggagttagccagaacgggcttagaaacagcaatt
121 ------------+---------+---------+---------+---------+---------+ 180
    tgaagtccagaagttgagggaactaccctcaatcggtcttgcccgaatctttgtcgttaa gatggcttagtgactgattttacaaatgatatttgtttcttcttttaaatttctttctagg
181 ------------+---------+---------+---------+---------+---------+ 240
    ctaccgaatcactgactaaaatgtttactataaacaaagaagaaatttaaagaaagatcc M  N  E  C  H  Y  D  K  H  M  D  F  F  Y
    atgttcacttCTTCTCCACAATGAATGAGTGTCACTATGACAAGCACATGGACTTTTTTT
241 ------------+---------+---------+---------+---------+---------+ 300
    tacaagtgaagaagAGGTGTTACTTACTCACAGTGATACTGTTCGTGTACCTGAAAAAAA N  R  S  N  T  D  T  V  D  D  W  T  G  T  K  L  V  I  V  L
    ATAATAGGAGCAACACTGATACTGTCGATGACTGGACAGGAACAAAGCTTGTGATTGTTT
301 ------------+---------+---------+---------+---------+---------+ 360
    TATTATCCTCGTTGTGACTATGACAGCTACTGACCTGTCCTTGTTTCGAACACTAACAAA
```

Fig. 4B

```
           C  V  G  T  F  F  C  L  F  I  F  F  S  N  S  L  V  I  A  A
       TGTGTGTTGGGACGTTTTTCTGCCTGTTTATTTTTTTTTCTAATTCTCTGGTCATCGCGG
361    ---------+---------+---------+---------+---------+---------+    420
       ACACACAACCCTGCAAAAAGACGGACAAATAAAAAAAAAGATTAAGAGACCAGTAGCGCC

V  I  K  N  R  K  F  H  F  P  F  Y  Y  L  L  A  N  L  A  A
       CAGTGATCAAAAACAGAAAATTTCATTTCCCCTTTTACTACCTGTTGGCTAATTTAGCTG
421    ---------+---------+---------+---------+---------+---------+    480
       GTCACTAGTTTTTGTCTTTTAAAGTAAAGGGGAAAATGATGGACAACCGATTAAATCGAC

A  D  F  F  A  G  I  A  Y  V  F  L  M  F  N  T  G  P  V  S
       CTGCCGATTTCTTCGCTGGAATTGCCTATGTATTCCTGATGTTTAACACAGGCCCAGTTT
481    ---------+---------+---------+---------+---------+---------+    540
       GACGGCTAAAGAAGCGACCTTAACGGATACATAAGGACTACAAATTGTGTCCGGGTCAAA

K  T  L  T  V  N  R  W  F  L  R  Q  G  L  L  D  S  S  L  T
       CAAAAACTTTGACTGTCAACCGCTGGTTTCTCCGTCAGGGGCTTCTGGACAGTAGCTTGA
541    ---------+---------+---------+---------+---------+---------+    600
       GTTTTTGAAACTGACAGTTGGCGACCAAAGAGGCAGTCCCCGAAGACCTGTCATCGAACT
```

Fig. 4C

```
         A  S  L  T  N  L  L  V  I  A  V  E  R  H  M  S  I  M  R  M
      CTGCTTCCCTCACCAACTTGCTGGTTATCGCCGTGGAGAGGCACATGTCAATCATGAGGA
601   ------------+----------+----------+----------+----------+----------+  660
      GACGAAGGGAGTGGTTGAACGACCAATAGCGGCACCTCTCCGTGTACAGTTAGTACTCCT

R  V  H  S  N  L  T  K  K  R  V  T  L  L  I  L  L  V  W  A
      TGCGGGTCCATAGCAACCTGACCAAAAAGAGGGTGACACTGCTCATTTTGCTTGTCTGGG
661   ------------+----------+----------+----------+----------+----------+  720
      ACGCCCAGGTATCGTTGGACTGGTTTTTCTCCCACTGTGACGAGTAAAACGAACAGACCC

I  A  I  F  M  G  A  V  P  T  L  G  W  N  C  L  C  N  I  S
      CCATCGCCATTTTTATGGGGGCGGTCCCCACACTGGGCTGGAATTGCCTCTGCAACATCT
721   ------------+----------+----------+----------+----------+----------+  780
      GGTAGCGGTAAAAATACCCCCGCCAGGGGTGTGACCCGACCTTAACGGAGACGTTGTAGA

A  C  S  S  L  A  P  I  Y  S  R  S  Y  L  V  F  W  T  V  S
      CTGCCTGCTCTTCCCTGGCCCCCATTTACAGCAGGAGTTACCTTGTTTTCTGGACAGTGT
781   ------------+----------+----------+----------+----------+----------+  840
      GACGGACGAGAAGGGACCGGGGGTAAATGTCGTCCTCAATGGAACAAAAGACCTGTCACA

N  L  M  A  F  L  I  M  V  V  V  Y  L  R  I  Y  V  Y  V  K
      CCAACCTCATGGCCTTCCTCATCATGGTTGTGGTGTACCTGCGGATCTACGTGTACGTCA
841   ------------+----------+----------+----------+----------+----------+  900
      GGTTGGAGTACCGGAAGGAGTAGTACCAACACCACATGGACGCCTAGATGCACATGCAGT

R  K  T  N  V  L  S  P  H  T  S  G  S  I  S  R  R  R  T  P
      AGAGGAAAACCAACGTCTTGTCTCCGCATACAAGTGGGTCCATCAGCCGCCGGAGGACAC
901   ------------+----------+----------+----------+----------+----------+  960
      TCTCCTTTTGGTTGCAGAACAGAGGCGTATGTTCACCCAGGTAGTCGGCGGCCTCCTGTG

M  K  L  M  K  T  V  M  T  V  L  G  A  F  V  V  C  W  T  P
      CCATGAAGCTAATGAAGACGGTGATGACTGTCTTAGGGGCGTTTGTGGTATGCTGGACCC
961   ------------+----------+----------+----------+----------+----------+  1020
      GGTACTTCGATTACTTCTGCCACTACTGACAGAATCCCCGCAAACACCATACGACCTGGG
```

Fig. 4D

```
          G  L  V  V  L  P  L  D  G  L  N  C  R  Q  C  G  V  Q  H  V
        CGGGCCTGGTGGTTCTGCCCCTCGACGGCCTGAACTGCAGGCAGTGTGGCGTGCAGCATG
1021    ----------+---------+---------+---------+---------+---------+ 1080
        GCCCGGACCACCAAGACGGGGAGCTGCCGGACTTGACGTCCGTCACACCGCACGTCGTAC

K  R  W  F  L  L  L  A  L  L  N  S  V  V  N  P  I  I  Y  S
        TGAAAAGGTGGTTCCTGCTGCTGGCGCTGCTCAACTCCGTCGTGAACCCCATCATCTACT
1081    ----------+---------+---------+---------+---------+---------+ 1140
        ACTTTTCCACCAAGGACGACGACCGCGACGAGTTGAGGCAGCACTTGGGGTAGTAGATGA

Y  K  D  E  D  M  Y  G  T  M  K  K  M  I  C  C  F  S  Q  E
        CCTACAAGGACGAGGACATGTATGGCACCATGAAGAAGATGATCTGCTGCTTCTCTCAGG
1141    ----------+---------+---------+---------+---------+---------+ 1200
        GGATGTTCCTGCTCCTGTACATACCGTGGTACTTCTTCTACTAGACGACGAAGAGAGTCC

N  P  E  R  R  P  S  R  I  P  S  T  V  L  S  R  S  D  T  G
        AGAACCCAGAGAGGCGTCCCTCTCGCATCCCCTCCACAGTCCTCAGCAGGAGTGACACAG
1201    ----------+---------+---------+---------+---------+---------+ 1260
        TCTTGGGTCTCTCCGCAGGGAGAGCGTAGGGGAGGTGTCAGGAGTCGTCCTCACTGTGTC

S  Q  Y  I  E  D  S  I  S  Q  G  A  V  C  N  K  S  T  S  *
        GCAGCCAGTACATAGAGGATAGTATTAGCCAAGGTGCAGTCTGCAATAAAAGCACTTCCT
1261    ----------+---------+---------+---------+---------+---------+ 1320
        CGTCGGTCATGTATCTCCTATCATAATCGGTTCCACGTCAGACGTTATTTTCGTGAAGGA
```

Fig. 4E

```
       AAACTCTGGATGCCTCTYGGCCCACCCAGGCCTCCTCTGGGAAAAGAGCTGTTAAGAATG
1321   ------------+---------+---------+---------+---------+---------+ 1380
       TTTGAGACCTACGGAGARCCGGGTGGGTCCGGAGGAGACCCTTTTCTCGACAATTCTTAC

ATTACCTGTCTCTAACAAAGCCCATGTACAGTGTTATTTGAGGTCTCCATTAATCACTGC
1381   ------------+---------+---------+---------+---------+---------+ 1440
       TAATGGACAGAGATTGTTTCGGGTACATGTCACAATAAACTCCAGAGGTAATTAGTGACG

TAGATTTCTTTAAAAAATTTTTTTTCATAGTTTAAAAGCATGGGCAGTAAAGAGAGGACC
1441   ------------+---------+---------+---------+---------+---------+ 1500
       ATCTAAAGAAATTTTTTAAAAAAAAGTATCAAATTTTCGTACCCGTCATTTCTCTCCTGG

TGCTGCATTTAGAGAAAGCACAG
1501   ---------+---------+--- 1523
       ACGACGTAAATCTCTTTCGTGTC
```

MAMMALIAN EDG-5 RECEPTOR HOMOLOGS

FIELD OF THE INVENTION

The present invention is in the field of molecular biology; more particularly, the present invention describes a nucleic acid sequence and an amino acid sequence for novel mammalian, including human, EDG-5 receptor homologs.

BACKGROUND OF THE INVENTION

The family of edg receptors are commonly grouped with orphan receptors because their endogenous ligands are not known (for example see Hla T and Maciag T (1990) J Biol. Chem. 265:9308–13; U.S. Pat. No. 5,585,476). Recently, however, lysophospatidic acid has been demonstrated to be the endogenous ligand for the edg-2 receptor (Hecht et al. (1996) J. Cell. Biol. 135: 1071–1083; An et al. (1997) Biochem. Biophys. Res. Comm. 213: 619–622).

The edg family of receptors are seven transmembrane G protein coupled receptors (T7Gs). T7Gs are so named because of their seven hydrophobic domains which span the plasma membrane and form a bundle of antiparallel a helices. These transmembrane segments (TMS) are designated by roman numerals I–VII and account for structural and functional features of the receptor. In most cases, the bundle of helices forms a binding pocket; however, when the binding site must accommodate more bulky molecules, the extracellular N-terminal segment or one or more of the three extracellular loops participate in binding and in subsequent induction of conformational change in intracellular portions of the receptor. The activated receptor, in turn, interacts with an intracellular G-protein complex which mediates further intracellular signaling activities generally the production of second messengers such as cyclic AMP (cAMP), phospholipase C, inositol triphosphate, activation of protein kinases, alteration in the expression of specific genes.

T7G receptors are expressed and activated during numerous developmental and disease processes. Identification of a novel T7G receptor provides the opportunity to diagnose or intervene in such processes, and the receptor can be used in screening assays to identify physiological or pharmaceutical molecules which trigger, prolong or inhibit its activity or differentially modulate distinct intracellular pathways which are controlled from T7G receptors.

SUMMARY OF THE INVENTION

The invention provides unique nucleotide sequences which encode novel mammalian, including human EDG-5 (HEDG) receptor homologs. Herein, the nucleotide sequence encoding HEDG is designated hedg.

The invention relates to the use of nucleic acid and amino acid sequences of mammalian edg-5, and more particularly, to the use of hedg, or its variants, in the diagnosis or treatment of diseased cells and/or tissues associated with aberrant expression of hedg. Aspects of the invention include the antisense DNA of hedg; cloning or expression vectors containing hedg; host cells or organisms transformed with expression vectors containing hedg; chromosomal localization of hedg; expression and tissue distribution of hedg; a method for the production and recovery of purified HEDG from host cells; purified protein, HEDG, which can be used to identify inhibitors for the downregulation of signal transduction involving HEDG; and methods of screening for ligands of hedg using transformed cells.

BRIEF DESCRIPTION OF THE DRAWINGS

FIG. 1 shows SEQ ID NO: 3, a partial DNA sequence of clone 501 which is a murine edg-5.

FIG. 2 shows SEQ ID NO: 15, the amino acid sequence encoded by the DNA sequence of FIG. 1 X represents an amino acid which cannot be assigned due to poor sequencing information from direct PCR sequencing.

FIG. 3 shows SEQ ID NO: 13, a nucleotide sequence of hedg cDNA inserted into pcDNA3, nucleotides 36–1907 of which encode the full length HEDG. Start and stop codons are underlined.

DETAILED DESCRIPTION OF THE INVENTION

Figure 4:
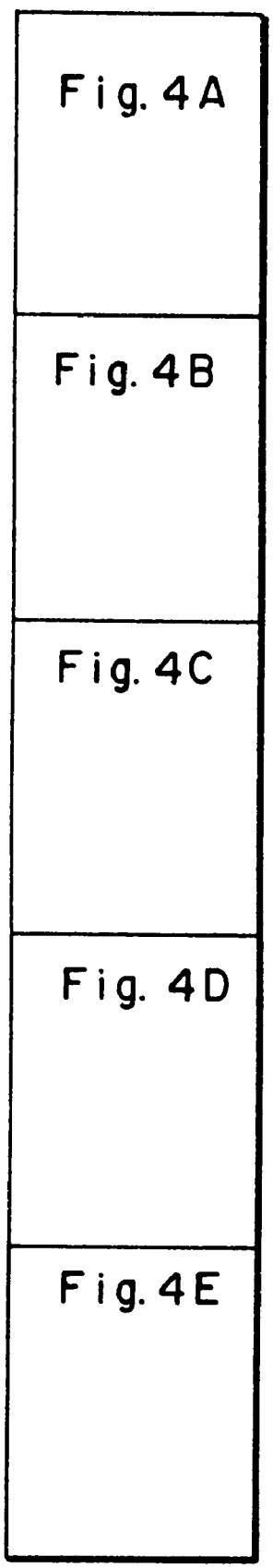
FIG. 4 shows an alignment of the hedg cDNA of FIG. 3 with the predicted amino acid sequence SEQ ID NO: 14. The DNA sequence depicted in FIG. 4 is SEQ ID NO: 12. The first 250 bp of DNA sequence (lower case) is derived from genomic DNA flanking the 5' end of the cDNA insert from clone pC3-hEdg5. Sequences from nt 251–253 are shown in lower case wherever apparent polymorphisms in different human clones were found. Coding region polymorphisms in different human clones were found. One intron exists within the coding region of hedg, located between nt 996/997 of the cDNA sequence shown.

The invention relates in one respect to polynucleotides, in their isolated form, that code for mammalian, including human, EDG-5 receptors. As used herein "isolated" means separated from polynucleotides that encode other proteins. In the context of polynucleotide libraries, for instance, A EDG-5 receptor-encoding polynucleotide is considered "isolated" when it has been selected, and hence removed from association with other polynucleotides within the library. Such polynucleotides may be in the form of RNA, or in the form of DNA including cDNA, genomic DNA and synthetic DNA. The EDG-5 receptors are characterized by structural features common to the G-protein coupled receptor class, including seven transmembrane regions, and by the functional properties of binding lysophospholipid selectively. When expressed functionally in a host cell, i.e., in operable linkage with a responsive second messenger system the EDG-5 receptors are capable further of responding to lysophospholipid binding by signal transduction. In this regard, the activity of a G-protein coupled receptor such as a EDG-5 receptor can be measured using any of a variety of appropriate functional assays described hereinbelow.

The novel murine hedg sequence was isolated following PCR from a murine neuronal cell line using degenerate primers based on conserved regions of transmembrane domains (TM-2) and TM-7 of G protein-coupled receptor (GPCR) superfamily. Sequence comparison with known sequences demonstrated that this; mouse clone represented a gene related to, but not indentical to edg-2, an orphan GPCR. Sequence identity was 49% at the nucleotide level. In the studies detailed herein the hedg sequence was used, however, these studies and the applications detailed herein could be undertaken using the novel mouse edg-5 sequence disclosed herein.

As used herein and designated by the upper case abbreviation, HEDG, refers to a human EDG-5 receptor homolog in either naturally occurring or synthetic form and active fragments thereof which have the amino acid sequence of SEQ. ID NO:14; FIG. 4. In one embodiment, the polypeptide HEDG is encoded by mRNAs transcribed from the cDNA, as designated by the lower case abbreviation, hedg, of SEQ. ID NO:12.

The novel human EDG-5 receptor homolog, HEDG, was cloned and isolated from a human fetal heart λgt10 cDNA library (Clontech., Cat. HL5017a), following PCR amplification of a partial human edg-5 gene from human genomic DNA (Promega Catalog. G304A) using PCR primers based on the partial mouse hedg sequence.

The full length mouse sequence can be obtained using method well known to those of skill in the art. For example, by screening an arrayed mouse library (Genome Systems Inc.) using the full-length human edg-5 cDNA. The hedg sequence is first radiolabelled using the condon priming method and then hybridized to the PAC filters and washed at high stringency, with the final wash done for 30 min at 65° C. in 1× SSC. Genomic DNA inserts from the clones with the strongest signals can be shotgun subcloned into pBluescript or a comparable cloning vector, using at least 3 different restriction digests of which 1 should have a 4 bp recognition site. Each digest yields a different subclone library, which in turn can be screened with the same cDNA probe under the same stringency conditions. Positives are picked, grown, mapped by restriction digest and Southern blotting to identify the size of the hybridizing insert, then sequenced using primers based on either the vector sequence, or on human edg-5 sequences. The position of the single intron seen in the human edg-5 gene should be conserved in the mouse gene. Thus, primers can be designed with a high degree of confidence to obtain the complete coding sequence of the mouse edg-5 gene without including intron sequences. Once the coding region has been determined, new PCR primers can be designed to amplify the cDNA directly from various tissue and/or cell line sources. A more detailed description of this approach can be found in Mannaitis et al. Molecular Cloning, a Laboratory Manual (Cold Spring Harbor Press, 1989).

An "oligonucleotide" is a stretch of nucleotide residues which has a sufficient number of bases to be used as an oligomer, amplimer or probe in a polymerase chain reaction (PCR). Oligonucleotides are prepared from genomic or cDNA sequence and are used to amplify, reveal or confirm the presence of a similar DNA or RNA in a particular cell or tissue. Oligonucleotides or oligomers comprise portions of a DNA sequence having at least about 10 nucleotides and as many as about 35 nucleotides, preferably about 25 nucleotides.

"Probes" may be derived from naturally occurring or recombinant single—or double—stranded nucleic acids or be chemically synthesized. They are useful in detecting the presence of identical or similar sequences.

A "portion" or "fragment" of a polynucleotide or nucleic acid comprises all or any part of the nucleotide sequence having fewer nucleotides than about 6 kb, preferably fewer than about 1 kb which can be used as a probe. Such probes may be labeled with reporter molecules using nick translation, Klenow fill-in reaction, PCR or other methods well known in the art. After protesting to optimize reaction conditions and to eliminate false positives, nucleic acid probes may be used in southern, northern or in situ hybridizations to determine whether DNA or RNA encoding HEDG is present in a cell type, tissue, or organ. "Reporter" molecules are those radionuclides, enzymes, fluorescent, chemiluminescent, or chromogenic agents which associate with, establish the presence of, and may allow quantification of a particular nucleotide or amino acid sequence.

"Recombinant nucleotide variants" encoding HEDG may be synthesized by making use of the "redundancy" in the genetic code. Various codon substitutions, such as the silent changes which produce specific restriction sites or codon usage-specific mutations, may be introduced to optimize cloning into a plasmid or viral vector or expression in a particular prokaryotic or eukaryotic host system respectively a "Chimeric" molecules may be constructed by introducing all or part of the nucleotide sequence of this invention into a vector containing additional nucleic acid sequence which might be expected to change any one (or more than one) of the following HEDG characteristics: cellular location, distribution, ligand-binding affinities, interchain affinities, degradation/turnover rate, signaling, etc.

"Active" refers to those forms, fragments, or domains of any HEDG polypeptide which retain the biological and/or antigenic activities of any naturally occurring HEDG.

"Naturally occurring HEDG" refers to a polypeptide produced by cells which have not been genetically engineered and specifically contemplates various polypeptides arising from post-translations modifications of the polypeptide including but not limited to acetylation, carboxylation, glycosylation, phosphorylation, lipidation and acylation.

"Derivative" refers to those polypeptides which have been chemically modified by such techniques as ubiquitination, labeling (see above), pegylation (derivatization with polyethylene glycol), and chemical insertion or substitution of amino acids such as ornithine which do not normally occur in human proteins.

"Recombinant polypeptide variant" refers to any polypeptide which differs from naturally occurring HEDG by amino acid insertions, deletions and/or substitutions, created using recombinant DNA techniques. Guidance in determining which amino acid residues may be replaced, added or deleted without abolishing activities of interest may be found by comparing the sequence of HEDG with that of related polypeptides and minimizing the number of amino acid sequence changes made in highly conserved regions.

Amino acid "substitutions" are conservative in nature when they result from replacing one amino acid with another having similar structural and/or chemical properties, such as the replacement of a leucine with an isoleucine or valine, an aspartate with a glutamate, or a threonine with a serine.

"Insertions" or "deletions" are typically in the range of about 1 to 5 amino acids. The variation allowed may be experimentally determined by producing the peptide synthetically or by systematically making insertions, deletions, or substitutions of nucleotides in the hedg sequence using recombinant DNA techniques.

A "signal or leader sequence" can be used, when desired, to direct the polypeptide through a membrane of a cell. Such a sequence may be naturally present on the polypeptides of the present invention or provided from heterologous sources by recombinant DNA techniques.

An "oligopeptide" is a short stretch of amino acid residues and may be expressed from an oligonucleotide. It may be functionally equivalent to and the same length as (or considerably shorter than) a "fragment", "portion", or "segment" of a polypeptide. Such sequences comprise a stretch of amino acid residues of at least about 5 amino acids and often about 17 or more amino acids, typically at least about 9 to 13 amino acids, and of sufficient length to display biological and/or antigenic activity.

"Inhibitor" is any substance which retards or prevents a chemical or physiological reaction or response. Common inhibitors include but are not limited to antisense molecules, antibodies, and antagonists.

"Standard" expression is a quantitative or qualitative measurement for comparison. It is based on a statistically appropriate number of normal samples and is created to use as a basis of comparison when performing diagnostic assays, running clinical trials, or following patient treatment profiles.

"Animal" as used herein may be defined to include human, domestic (cats dogs, etc.), agricultural (cows, horses, sheep, etc.) or test species (mouse, rat, rabbit, etc.).

The present invention provides a nucleotide sequence uniquely identifying novel mammalian, including human (HEDG), seven transmembrane receptor (T7G) or EDG-5. Based on the homology of HEDG to human edg-2 (see table 2 below) it is likely that HEDG binds a ligand of the same chemical class. Edg-2 specifically binds lysophosphatidic acid (LPA) which is a phospholipid. Phospholipids have been demonstrated to be important regulators cell activity, including mitogenisis (Xu et al. (1995) J. Cell. Physiol., 163: 441–450) and apoptosis, cell adhesion and regulation of gene expression. Specifically, for example, LPA elicits growth factor-like effects on cell proliferation (Moolenar (1996) J. Biol. Chem, 270: 12949–12952) and cell migration (Imamura et al. (1993) Biochem. Biophys. Res. Comm., 193: 497–503). It has also been suggested that LPA plays a role in wound healing and regeneration (Tigyi et al. (1992) J. Biol. Chem., 267: 21360–21367). Further, considerable circumstantial evidence indicates that phospholipids may be involved in various disease states including cancer (Imamura et al., (1993) Biochem. Biophys. Res. Comm., 193: 497–503); diseases having an inflammatory component (Fourcade et al. (1995), Cell, 80(6): 919–927, including adult respiratory distress, neurodegeneration (Jalink et al. (1993) Cell Growth Differ., 4: 247–255), rheumatoid arthritis (Natiarajan et al. (1995) J. Lipid Res., 36(9): 2005–2016), psoriasis and inflammatory bowel disease. Thus, the ligand for HEDG is likely to be a biologically important regulator of cell activity, and therefore aberrant expression of HEDG is likely to be associated with a chronic or acute disease states. Further, modulators of HEDG activity are likely to be useful in treatment or prevention of such disease states.

HEDG ligands are likely to be found among the phospholipid class of compounds or phosphorylated analogs of cannabinoid R. Therefore, preferably phospholipid molecules should be screened to identify HEDG ligands. More preferably, lysophospholipds should be screened, for example the lysosphingolipids derivatives of cerebrosides, gangliosides and ceramide 1-phosphate. Even more preferably, lysoglycerophospholipids should be screened. Most preferably, LPA, lysophosphatidylethanolamine (LPE), lysophosphatidylserine (LPS), lysophosphatidylinositol (LPI), lysophosphatidylcholine (LPC), lyso-platelet activating factor (lyso-PAF) and phosphatidic acid should be screened. These ligands can be altered to improve metabolic stability, for example, by changing ester bond at Sa-1 to an ether on by blocking the free hydroxyl group with methoxy or acetyl ester. Additional medicinal chemistry benefits may be derived from shortening the fatty acid chain or altering the positioning of the phosphate. LPA and related phospholipids have limited solubility in aqueous solution and have a tendency to be sticky. These problems may be alleviated in a number of ways. For example, preparation of fresh stock solutions (e.g., 10 mM) by dissolving the phospholipid in calcium-free PBS and fatty-acid free BSA. Sphingosine-1-phosphate (S-1P) is conveniently handled by preparing a 10 mM stock directly in 100% methanol. Other related phospholipids can be prepared, for example, in 100% ethanol or DM50

A diagnostic test for aberrant expression of HEDG can accelerate diagnosis and proper treatment of abnormal conditions of for example, the heart, kidney, lung and testis. Specific examples of conditions in which aberrant expression of HEDG may play a role include adult respiratory distress, asthma, rheumatoid arthritis, cardiac ischemia, acute pancreatitis, septic shock, psoriasis, acute cyclosporine nephrotoxicity and early diabetic glomerulopathy, as well as lung damage following exposure to cigarette smoke, asbestos or silica.

The nucleotide sequences encoding HEDG (or their complement) have numerous applications in techniques known to those skilled in the art of molecular biology. These techniques include use as hybridization probes, use in the construction of oligomers for PCR, use for chromosome and gene mapping, use in the recombinant production of HEDG, and use in generation of antisense DNA or RNA, their chemical analogs and the like. Uses of nucleotides encoding HEDG disclosed herein are exemplary of known techniques and are not intended to limit their use in any technique known to a person of ordinary skill in the art. Furthermore, the nucleotide sequences disclosed herein may be used in molecular biology techniques that have not yet been developed, provided the new techniques rely on properties of nucleotide sequences that are currently known, e.g., the triplet genetic code, specific base pair interactions, etc.

It will be appreciated by those skilled in the art that as a result of the degeneracy of the genetic code, a multitude of HEDG-encoding nucleotide sequences may be produced. Some of these will only bear minimal homology to the nucleotide sequence of the known and naturally occurring HEDG. The invention has specifically contemplated each and every possible variation of nucleotide sequence that could be made by selecting combinations based on possible codon choices. These combinations are made in accordance with the standard triplet genetic code as applied to the nucleotide sequence of naturally occurring hedg, and all such variations are to be considered as being specifically disclosed.

Although the nucleotide sequences which encode HEDG, its derivatives or its variants are preferably capable of hybridizing to the nucleotide sequence of the naturally occurring hedg under stringent conditions, it may be advantageous to produce nucleotide sequences encoding HEDG or its derivatives possessing a substantially different codon usage. Codons can be selected to increase the rate at which expression of the peptide occurs in a particular prokaryotic or eukaryotic expression host in accordance with the frequency with which particular codons are utilized by the host. Other reasons for substantially altering the nucleotide sequence encoding HEDG and/or its derivatives without altering the encoded aa sequence include the production of RNA transcripts having more desirable properties, such as a greater half-life, than transcripts produced from the naturally occurring sequence.

Nucleotide sequences encoding HEDG may be joined to a variety of other nucleotide sequences by means of well established recombinant DNA techniques (Sambrook J et al (1989) Molecular Cloning: A Laboratory Manual, Cold Spring Harbor Laboratory, Cold Spring Harbor N.Y.; or Ausubel FM et al (1989) Current Protocols in Molecular Biology, John Wiley & Sons, New York City). Useful nucleotide sequences for joining to hedg include an assortment of cloning vectors such as plasmids, cosmids, lambda phage derivatives, phagemids, and the like. Vectors of interest include expression vectors, replication vectors, probe generation vectors, sequencing vectors, etc. In general, vectors of interest may contain an origin of replication functional in at least one organism, convenient restriction endonuclease sensitive sites, and selectable markers for one or more host cell systems.

Another aspect of the subject invention is to provide for hedg-specific hybridization probes capable of hybridizing with naturally occurring nucleotide sequences encoding HEDG. Such probes may also be used for the detection of similar T7G encoding sequences and should preferably contain at least 56% nucleotide identity to hedg sequence. The hybridization probes of the subject invention may be derived from the nucleotide sequence presented as SEQ. ID NO:12 or from genomic sequences including promoter, enhancers or introns of the native gene. Hybridization probes may be labeled by a variety of reporter molecules using techniques well known in the art.

It will be recognized that many deletional or mutational analogs of nucleic acid sequences for HEDG will be effective hybridization probes for HEDG nucleic acid. Accordingly, the invention relates to nucleic acid sequences that hybridize with such HEDG encoding nucleic acid sequences under stringent conditions.

"Stringent conditions" refers to conditions that allow for the hybridization of substantially related nucleic acid sequences. For instance, such conditions will generally allow hybridization of sequence with at least about 80% sequence identity, preferably with at least about 90% sequence identity, more preferably with at least about 95% sequence identity. Such hybridization conditions are described by Sambrook et al., Molecular Cloning: A Laboratory Manual, 2nd ed., Cold Spring Harbor Press, 1989. Hybridization conditions and probes can be adjusted in well-characterized ways to achieve selective hybridization of human-derived probes. Nucleic acid molecules that will hybridize to HEDG encoding nucleic acid under stringent conditions can be identified functionally, using methods outlined above, or by using for example the hybridization rules reviewed in Sambrook et al., Molecular Cloning: A Laboratory Manual, 2nd ed., Cold Spring Harbor Press, 1989. Without limitation, examples of the uses for hybridization probes include: histochemical uses such as identifying tissues that express HEDG; measuring mRNA levels, for instance to identify a sample's tissue type or to identify cells that express abnormal levels of HEDG; and detecting polymorphisms in the HEDG. RNA hybridization procedures are described in Maniatis et al. Molecular Cloning, a Laboratory Manual (Cold Spring Harbor Press, 1989). PCR as described U.S. Pat. Nos. 4,683,195; 4,800,195; and 4,965,188 provides additional uses for oligonucleotides based upon the nucleotide sequence which encodes the edg-5 sequences of the invention. Such probes used in PCR may be of recombinant origin, chemically synthesized, or a mixture of both. Oligomers may comprise discrete nucleotide sequences employed under optimized conditions for identification of hedg in specific tissues or diagnostic use. The same two oligomers, a nested set of oligomers, or even a degenerate pool of oligomers may be employed under less stringent conditions for identification of closely related DNA's or RNA's. Rules for designing PCR primers are now established, as reviewed by PCR Protocols, Cold Spring Harbor Press, 1991. Degenerate primers, i.e., preparations of primers that are heterogeneous at given sequence locations, can be designed to amplify nucleic acid sequences that are highly homologous to, but not identical to hedg. Strategies are now available that allow for only one of the primers to be required to specifically hybridize with a known sequence. See, Froman et al., Proc. Natl. Acad. Sci. USA 85: 8998, 1988 and Loh et al., Science 243: 217, 1989. For example, appropriate nucleic acid primers can be ligated to the nucleic acid sought to be amplified to provide the hybridization partner for one of the primers. In this way, only one of the primers need be based on the sequence of the nucleic acid sought to be amplified. PCR methods of amplifying nucleic acid will utilize at least two primers. One of these primers will be capable of hybridizing to a first strand of the nucleic acid to be amplified and of priming enzyme-driven nucleic acid synthesis in a first direction. The other will be capable of hybridizing the reciprocal sequence of the first strand (if the sequence to be amplified is single stranded, this sequence will initially be hypothetical, but will be synthesized in the first amplification cycle) and of priming nucleic acid synthesis from that strand in the direction opposite the first direction and towards the site of hybridization for the first primer. Conditions for conducting such amplifications, particularly under preferred stringent hybridization conditions, are well known. See, for example, PCR Protocols, Cold Spring Harbor Press, 1991.

Other means of producing specific hybridization probes for hedg include the cloning of nucleic acid sequences encoding HEDG or HEDG derivatives into vectors for the production of mRNA probes. Such vectors are known in the art, are commercially available and may be used to synthesize RNA probes in vitro by means of the addition of the appropriate RNA polymerase as T7 or SP6 RNA polymerase and the appropriate reporter molecules.

It is possible to produce a DNA sequence, or portions thereof, entirely by synthetic chemistry. After synthesis, the nucleic acid sequence can be inserted into any of the many available DNA vectors and their respective host cells using techniques which are well known in the art. Moreover, synthetic chemistry may be used to introduce mutations into the nucleotide sequence. Alternately, a portion of sequence in which a mutation is desired can be synthesized and recombined with longer portion of an existing genomic or recombinant sequence.

The nucleotide sequence for hedg can be used in an assay to detect inflammation or disease associated with abnormal levels of HEDG expression. The cDNA can be labeled by methods known in the art, added to a fluid, cell or tissue sample from a patient, and incubated under hybridizing conditions. After an incubation period, the sample is washed with a compatible fluid which optionally contains a reporter molecule. After the compatible fluid is rinsed off, the reporter molecule is quantitated and compared with a standard as previously defined.

The nucleotide sequence for hedg has been used to construct hybridization probes for mapping the native gene. The edg-5 gene was mapped to a band p22.3 of chromosome 1 using bacterial artificial chromosomes isolated (BACs), as detailed in Example 14. Thus, the invention provides expression products from this locus that hybridize with hedg (SEQ ID NO:12) under stringent conditions. In situ hybridization of chromosomal preparations and physical mapping techniques such as linkage analysis using established chromosomal markers are invaluable in extending genetic maps. Examples of genetic map data can be found in the yearly genome issue of Science (e.g. 1994, 265:1981f).

New nucleotide sequences can be assigned to chromosomal subregions by physical mapping. The mapping of new genes or nucleotide sequences provide useful landmarks for investigators searching for disease genes using positional cloning or other gene discovery techniques. Once a disease or syndrome, such as ataxia telangiectasia (AT), has been crudely localized by genetic linkage to a particular genomic region, for example, AT to 1 1q22-23 (Gatti et al (1988) Nature 336:577–580), any sequences mapping to that area may represent or reveal genes for further investigation. The nucleotide sequence of the subject invention may also be used to detect differences in gene sequence between normal and carrier or affected individuals.

Nucleotide sequences encoding hedg may be used to produce a purified oligo—or polypeptide using well known methods of recombinant DNA technology. Goeddel (1990, Gene Expression Technology, Methods and Enzymology, Vol. 185, Academic Press, San Diego Calif.) is one among many publications which teach expression of an isolated nucleotide sequence. The oligopeptide may be expressed in a variety of host cells, either prokaryotic or eukaryotic. Host cells may be from the same species from which the nucleotide sequence was derived or from a different species. Advantages of producing an oligonucleotide by recombinant DNA technology include obtaining adequate amounts of the protein for purification and the availability of simplified purification procedures.

Cells transformed with DNA encoding HEDG may be cultured under conditions suitable for the expression of T7Gs, their extracellular, transmembrane or intracellular domains and recovery of such peptides from cell culture. HEDG (or any of its domains) produced by a recombinant cell may be secreted or may be contained intracellularly, depending on the particular genetic construction used. In general, it is more convenient to prepare recombinant proteins in secreted form. Purification steps vary with the production process and the particular protein produced. Often an oligopeptide can be produced from a chimeric nucleotide sequence. This is accomplished by ligating the nucleotides from hedg or a desired portion of the polypeptide to a nucleic acid sequence encoding a polypeptide domain which will facilitate protein purification (Kroll D J et al (1993) DNA Cell Biol. 12:441–53).

In addition to recombinant production, fragments of HEDG may be produced by direct peptide synthesis using solid-phase techniques (e.g. Stewart at al (1969) Solid-Phase Peptide Synthesis, WH Freeman Co., San Francisco QA; Merrifield J (1963) J Am Chem. Soc. 85:2149–2154). Automated synthesis may be achieved, for example, using Applied Biosystems 431A Peptide Synthesizer (Foster City, Calif.) in accordance with the instructions provided by the manufacturer. Additionally, a particular portion of HEDG may be mutated during direct synthesis and combined with other parts of the peptide using chemical methods.

HEDG for antibody induction does not require biological activity: however, the protein must be antigenic. Peptides used to induce specific antibodies may have an aa sequence consisting of at least five amino acids (aa), preferably at least 10 aa. They should mimic a portion of the aa sequence of the protein and may contain the entire aa sequence of a small naturally occurring molecule such as HEDG. An antigenic portion of HEDG may be fused to another protein such as keyhole limpet hemocyanin, and the chimeric molecule used for antibody production.

Antibodies specific for HEDG may be produced by inoculation of an appropriate animal with the polypeptide or an antigenic fragment. An antibody is specific for HEDG if it is produced against an epitope of the polypeptide and binds to at least part of the natural or recombinant protein. Antibody production includes not only the stimulation of an immune response by injection into animals, but also analogous processes such as the production of synthetic antibodies, the screening of recombinant immunoglobulin libraries for specific-binding molecules (e.g. Orlandi R et al (1989) PNAS 86:3833–3837, or Huse W D et al (1989) Science 256:1275–1281) or the in vitro stimulation of lymphocyte populations. Current technology (Winter G and MIstein C (1991) Nature 349:293–299) provides for a number of highly specific binding reagents based on the principles of antibody formation. These techniques may be adapted to produce molecules which specifically bind HEDGs.

An additional embodiment of the subject invention is the use of HEDG specific antibodies, inhibitors, ligands or their analogs as bioactive agents to treat inflammation or disease including, but not limited to viral, bacterial or fungal infections; allergic responses; mechanical injury associated with trauma; hereditary diseases; lymphoma or carcinoma; or other conditions which activate the genes of kidney, lung, heart, lymphoid or tissues of the nervous system.

Bioactive compositions comprising agonists, antagonists, receptors or inhibitors of HEDG may be administered in a suitable therapeutic dose determined by any of several methodologies including clinical studies on mammalian species to determine maximal tolerable dose and on normal human subjects to determine safe dose. Additionally, the bioactive agent may be complexed with a variety of well established compounds or compositions which enhance stability or pharmacological properties such as half-life. It is contemplated that the therapeutic, bioactive composition may be delivered by intravenous infusion into the bloodstream or any other effective means which could be used for treating problems involving aberrant expression of the Edg-5 gene.

The examples below are provided to illustrate the subject invention. These examples are provided by way of illustration and are not included for the purpose of limiting the invention.

EXAMPLES

Example 1

PCR Cloning of Murine EDG-5 cDNA

Poly-A+ RNA was isolated from TR and TSM murine neuronal cell lines by twice selecting on oligo-dT cellulose (Pharmacia, Cat. 27-5649-01). 10.5 $\mu$g of this RNA was reverse-transcribed with oligo-dT or random hexamers as to prime the RT reaction. RNA and primers were heated to 65° C. for 5 min., then cooled to room temperature. Additional reagents were added to give the following final concentrations: 50 mM Tris-Cl, pH 8.3, 6 mM MgCl$_2$, 40 mM KCl, 1 mM DTT, 1 mM each dNTP, and 1 unit/$\mu$l of Moloney murine virus RT enzyme.

First strand cDNA was amplified in PCR reactions using degenerate primers A1 (SEQ ID NO: 1) and A2 (SEQ ID NO: 2) was conducted as follows. PCR reactions used 40 ng of first strand cDNA in 10 mM Tris-Cl, pH 8.3, 50 mM KCl, 2 $\mu$M of each primer, 1.5 mM MgCl$_2$, 0.2 $\mu$M each dNTP and 2.5 units of Taq DNA polymerase. Thirty pairwise combinations of primers were used. Reactions were placed in a Perkin-Elmer 480 thermal cycler, denatured for 3 min. at 94° C., and then cycled 25–40 times at 96° C. for 45 sec, 47° C. for 144 sec or 53° C. for 216 sec, and 72° C. for 3 min. initially, increasing 6 sec/cycle. Products were cloned using the TA PCR cloning vector (Invitrogen, Cat. K2000-40). The resulting edg-5 clone, 501(SEQ ID NO: 3) was sequenced by the dideoxy termination method.

A1: 5'-AAYTRSATIMTISTIAAYYTIGCIGTIGCIGA-3' (SEQ ID NO: 1)

B1: 5'-CTGIYKWTTCATIAWIMMRTAIAYIAYIGGRTT-3' (SEQ ID NO: 2)

The sequence of clone 501(SEQ ID NO: 3) is shown in FIG. 1. An search of Genbank showed that clone 501 (SEQ ID NO: 3) was most closely related to the LPA receptor, also identified in Genbank as the GPCR orphan edg-2 (Genbank MMU 70622). Sequence identity between the clone 501 (SEQ ID NO: 3) and edg-2 was 60.5% over the 639 bp length of clone 501 (SEQ ID NO: 3).

Example 2

Isolation of HEDG cDNA

PCR Amplification of Partial hedg gene from Human Genomic DNA

PCR primers JC501-F2 (SEQ ID NO: 4) and JC501-R (SEQ ID NO: 5) were designed using the sequence of clone 501 (SEQ ID NO: 3) and used to obtain a PCR fragment of hedg, as detailed below with the Expand™ PCR system from Boehringer Mannheim (Cat. 1681-842). Human genomic DNA was obtained from Promega (Cat. G304A).

JC501-F2:
5'-TTTTTACTCGAGATTTGCTGGTTATTGCTGTGGAAAG-3' (SEQ ID NO: 4)

JC501-R:
5'-TTTTTTCTAGACGGTCATCACTGTCTTCATTAGCTTC-3' (SEQ ID NO: 5)

Each reaction contained the following reagents:

| | |
|---|---|
| 30.25 µl | water |
| 10 µl | 2.5 mM dNTP mix |
| 5 µl | 10x Expand ™ Buffer 3 |
| 1.5 µl | 10 µM JC501-F2 primer |
| 1.5 µl | 10 µM JC501-R primer |
| 0.75 µl | Expand PCR enzyme (3.5 units/µl) |
| 1 µl | human genomic DNA (0.272 µg/µl) |

PCR Conditions:
Incubate: 94° C. for 2 min.
30 cycles: 92° C. for 1 min.
　45° C. for 5min.
　68° C. for 1 min.
Hold: 4° C.

On ethidium bromide (EtBr)-stained agarose gel, an intense PCR product of about 390 bp was seen. This product was reamplified in the following PCR reaction:

| | |
|---|---|
| 30.25 µl | water |
| 10 µl | 2.5 mM dNTP mix |
| 5 µl | 10x Expand ™ Buffer 3 |
| 1.5 µl | 10 µM JC501-F2 primer |
| 1.5 µl | 10 µM JC501-R primer |
| 0.75 µl | Expand PCR enzyme (3.5 units/µl) |
| 1 µl | PCR product from the previous PCR reaction |

PCR Conditions:
Incubate: 94° C. for 2 min.
30 cycles: 92° C. for 1 min.
　45° C. for 5 min.
　68° C. for 1 min.
Hold: 4° C.

The intense 390 bp product of the PCR reamplification was excised from the agarose gel. The PCR products from 30 µl of the PCR reaction were purified from pooled gel slices using a Qiaquick Gel extraction kit (Qiagen Inc.; Cat. 28706) and eluted with 20 µl of 10 mM Tris-Cl, pH 8.5. The eluted DNA was quantitated and the sequence of the PCR product was determined by automated sequencing at Allelix's in-house facility, with an ABI 377 Sequencer and fluorescent dideoxy terminators, using each primer from the PCR reactions shown above.

Sequencing results showed 81.5% identity at the nucleotide level with the sequence of mouse clone 501, over a 312 bp overlap excluding the primer sequences.

PCR Amplification and Sequencing of Large edg-5 CDNA Fragments

Primers, H501-20F (SEQ ID NO: 6) and H501-246R (SEQ ID NO: 7), specific to hedg, were used to amplify cDNAs encoding larger portions of hedg form a 1gt10 fetal heart cDNA library, as follows.

H501-20F:
5'-ATGCGGCTGCATAGCAACCTGACCAAAAAG-3' (SEQ ID NO: 6)

H501-246R:
5'-ATCCGCAGGTACACCACAACCATGATGAGG-3' (SEQ ID NO: 7)

Each reaction contained the following reagents:

| | |
|---|---|
| 30.25 µl | water |
| 10 µl | 2.5 mM dNTP mix |
| 5 µl | 10x Expand ™ Buffer 3 |
| 1.5 µl | 10 µM H501-20F primer |
| 1.5 µl | 10 µM H501-246R primer |
| 0.75 µl | Expand PCR enzyme (3.5 units/µl) |
| 1 µl | fetal heart cDNA library (≧1 library equivalent/µl; Clontech; Cat. HL5017a) |

PCR Conditions:
Incubate: 94° C. for 2 min.
30 cycles: 92° C. for 1 min.
　45° C. for 5 min.
　68° C. for 1.5 min.
Incubate: 68° C. for 8 min.
Hold: 4° C.

On EtBr-stained agarose gel, a moderately intense 250 bp PCR product was seen in a fetal heart library, the approximate size expected from the positions of the primers. No specific PCR products were seen in any of 13 other cDNA libraries tested.

To obtain additional edg-5 sequence, and possibly amplify the full-length cDNA from the fetal heart cDNA library, PCR reactions were conducted using JC501-F2 (SEQ ID NO: 4) or JC501-R (SEQ ID NO: 5) primers versus primers derived from the 1gt10 vector in which this cDNA library was constructed. Although cDNA inserts are not directionally cloned into the 1gt10 vector, we chose to amplify products only from one direction. The vector-based primer sequences were:

GT10-F: 5'-TTTTGAGCAAGTTCAGCCTGGTTAAGT-3' (SEQ ID NO: 8)

GT10-R: 5'-TGGCTTATGAGTATTTCTTCCAGGGTA-3' (SEQ ID NO: 9)

One PCR reaction was done with JC501-F2 (SEQ ID NO: 4) vs. GT10-R (SEQ ID NO: 9) primers to amplify the 3' end of edg-5 cDNA clones, and another was done with GT10-F (SEQ ID NO: 8) vs. JC501-R (SEQ ID NO: 5) primers to amplify the 5' end of edg-5 cDNA clones. Each 40 µl reaction contained the following reagents:

| | |
|---|---|
| 23.6 µl | water |
| 8.0 µl | 2.5 mM dNTP mix |
| 4 µl | 10x Expand ™ Buffer 3 |
| 2.0 µl | 10 µM edg-5 specific primer |
| 0.8 µl | 10 µM vector primer |
| 0.6 µl | Expand PCR enzyme (0.4 units) |
| 1 µl | cDNA library stock (≧1 library equivalent/µl; Clontech; Cat. HL5017a) |

PCR Conditions:
Incubate: 94° C. for 2 min.
30 cycles: 92° C. for 30 sec
　55° C. for 2 min.
　68° C. for 3 min.

Incubate: 68° C. for 8 min.
Hold: 4° C.

The results showed 2 faint PCR products (designated 510-5-1 and 510-5-2) from the 3'-end PCR reaction (JC501-F2 (SEQ ID NO:4/GT10-R (SEQ ID NO:9). From the 5'-end PCR reaction (GT10-F (SEQ ID NO:8)/JC501-R (SEQ ID NO:5) again 2 faint PCR bands (designated 510-6-1 and 510-6-2) were seen. Each band was tip-eluted from the gel by stabbing the band with a fresh Pipetman plugged tip, which was then rinsed into 50 µl of TE, pH 8. This solution was used as a stock from which nested reamplifications were done, using the same vector primer vs. a nested human-specific primer as follows:

| | |
|---|---|
| 11.5 µl | water |
| 4.0 µl | 2.5 mM dNTP mix |
| 2 µl | 10x Expand ™ Buffer 1 |
| 0.6 µl | 10 µM edg-5 specific primer |
| 0.6 µl | 10 µM vector primer |
| 0.3 µl | Expand PCR enzyme (0.4 units) |
| 1 µl | tip-eluted PCR DNA stock |

PCR Conditions:

Incubate: 94° C. for 2 min.
30 cycles: 92° C. for 30 sec
  55° C. for 40 sec
  68° C. for 3min.
Incubate: 68° C. for 8 min.
Hold: 4° C.

DNA from the most intense band of each nested reamplification was purified using a QIAquick Gel extraction kit and eluted in 50 ul of 10 mM Tris-Cl, pH 8.5.

Full-length Cloning of the hedg cDNA into pcDNA3 Vector

Extension PCR (cycles without primers) was used to extend the overlapping ~1.0 kb 3' fragment (designated 511-5: reamplified from 510-5-2) and 700 bp 5' fragment (designated 511-14: reamplified from 510-6-2) as follows:

Extension PCR:

| | |
|---|---|
| 19.8 µl | water |
| 5.6 µl | 2.5 mM dNTP mix |
| 4.0 µl | 10x Expand ™ Buffer 1 |
| 5 µl | edg-5 3' PCR DNA fragment (511-5) |
| 5 µl | edg-5 5' PCR DNA fragment (511-14) |
| 0.6 µl | Expand PCR enzyme (3.5 units/µl) |

PCR Conditions:

Incubate 94° C. for 2 min.
15 cycles: 92° C. for 1 min.
  60° C. for 10 min.
  68° C. for 3.5 min.
Incubate: 68° C. for 8 min.
Hold: 4° C.

Two microliters of the extension PCR reaction was then reamplified using the two vector primers (GT10-F (SEQ ID NO:8) and GT10-R (SEQ ID NO:9) to select for full-length extension products.

| | |
|---|---|
| 32.25 µl | water |
| 7.0 µl | 2.5 mM dNTP mix |
| 5.0 µl | 10x Expand ™ Buffer 1 |
| 1.5 µl | 10 µM GT10-F primer |
| 1.5 µl | 10 µM GT10-R primer |
| 0.75 µl | Expand PCR enzyme (3.5 units/µl) |

PCR Conditions:

Incubate 94° C. for 2 min.
30 cycles: 92° C. for 40 sec
  50° C. for 40 sec
  68° C. for 3 min.
Incubate: 68° C. for 8 min.
Hold: 4° C.

After gel electrophoresis of the PCR products, an intense DNA band of about 1.4 kb was seen. The PCR product was purified with a QIAquick PCR purification kit (QIAGEN Inc., Cat. 28106), eluted in 50 µl of 10 mM Tris-Cl, pH 8.5. The gel-purified PCR fragment was then sent for automated sequencing at Allelix's in-house facility, as described above. The sequencing results confirmed the identity of the amplified band as edg-5, and suggested that a full-length clone of edg-5 had been reconstructed by extension PCR.

To subclone into pcDNA3 the above DNA was reamplified with modified vector primers GT10-5KXb (SEQ ID NO: 10) and GT10-3BXh (SEQ ID NO: 11).

GT10-5KXb:
5'-GGGTAGTCGGTACCTCTAGAGCAAGTTCAGCC-3' (SEQ ID NO: 10)

GT10-3BXh:
5'-ATAACAGAGGATCCTCGAGTATTTCTTCCAG-3' (SEQ ID NO: 11)

Reamplification PCR:

| | |
|---|---|
| 67.5 µl | water |
| 14 µl | 2.5 mM dNTP mix |
| 10 µl | 10x Expand ™ Buffer 1 |
| 3 µl | 10 µM GT10-5KXb primer |
| 3 µl | 10 µM GT10-3BXh primer |
| 1.5 µl | Expand PCR enzyme (3.5 units/µl) |
| 1 µl | DNA from previous PCR reaction |

PCR Conditions:

Incubate 94° C. for 2 min.
5 cycles: 92° C. for 1 min.
  50° C. for 1 min.
  68° C. for 2 min.
25 cycles: 92° C. for 1 min.
  60° C. for 1 min.
  68° C. for 2 min.
Incubate: 68° C. for 8 min.
Hold: 4° C.

The PCR product was QIAquick PCR-purified and eluted in 50 µl of 10 mM Tris-Cl, pH 8.5 as described previously and restricted with KpnI and XhoI.

Restriction digest of PCR sample with KpnI and XhoI:

Two successive restriction digests was performed on the purified extension PCR product as follows:

```
38 µl  Extension PCR DNA
 5 µl  10X NEBuffer 1 (New England Biolabs [NEB])
 2 µl  KpnI restriction endonuclease (10 units; NEB, Cat #142S)
 5 µl  10X Acetylated BSA stock (NEB)
```

The restriction digest was incubated for 1 hour in a 37° C. water bath. and then the following reagents and enzyme were added:

```
10 µl  10X NEBuffer 2 (NEB)
 1 µl  XhoI restriction endonuclease (20 units; NEB, Cat #146S)
 5 µl  10X Acetylated BSA stock (NEB)
43 µl  water
```

The reaction products were purified using a QIAquick PCR purification kit and eluted in 50 µl of 10 mM Tris-Cl, pH 8.5.

Preparation of pcDNA3 cloning vector with KpnI and XhoI:

```
 4 µl  pcDNA3 plasmid DNA (Invitrogen; Cat. V790-20) containing
       a 1.8 kb cDNA insert
10 µl  10X NEBuffer 2 (NEB)
 3 µl  KpnI restriction endonuclease (NEB: 1:10 dilution; 3 units)
 3 µl  XhoI restriction endonuclease (NEB: 1:20 dilution; 3 units)
10 µl  10X Acetylated BSA stock (NEB)
64 µl  water
```

The vector DNA was digested for 1 hour at 37° C. Then, 3 units more of each enzyme was added and the tubes were incubated for a further 2 hr. The digest was run on a gel, and the vector DNA band without cDNA insert was excised, purified using GeneClean II kit (BIO 101) and eluted in 40 µl of 10 mM Tris-Cl, pH 8.5.

The double-digested, gel-purified PCR DNA was ligated into the prepared pcDNA3 plasmid vector using T4 DNA ligase kit (NEB, Cat. 202CS) and transformed into Epicurean Coli XL-2 Blue MRF' Ultracompetent cells (Stratagene, Cat. 200150). The transformation was plated onto 2xYT/Ampicillin plates and single colonies were picked. DNA minipreps were made using QIAGEN QIA-Prep8 miniprep kit (Cat. 27144) and clones with appropriate inserts were identified by sequencing, carried out with the in-house ABI automated sequencing system. From this analysis, a clone designated pC3-hEdg5-3 (SEQ ID NO:12) was chosen for complete sequence determination of the cDNA insert.

Features of the hedg cDNA

A BLAST search of Genbank, EMBL, dbEST, and the GSS and STS genomic sequencing databases indicates that the hedg sequence is novel. The bovine LPA receptor, edg-2, was the highest-scoring full-length cDNA sequence found from the combined Genbank/EMBL databases (Genbank BTU48236: 55% identity).

This sequence includes 10 bp of 5'-untranslated sequence, the edg-5 open reading frame of 1059 bp, and a 3'-untranslated region spanning 204 bp. The coding region of edg-5 begins with the first methionine codon, at nt 36–38 and terminates with the stop codon at nt 1095–1097. The prediction of this open reading frame is supported by the sequence of genomic DNA flanking the 5' end of the cDNA sequence (see below). 250 bp of 5' flanking sequence was obtained from a BAC genomic clone as described in Example 14 (FIG. 4). The proposed translation start site was preceded by an in-frame stop codon 24 bp upstream. Sequencing of different clones revealed the existence of several sequence polymorphisms, which may represent a sampling of natural variability of the edg-5 sequence within the human population. The 15 polymorphisms observed within the edg-5 open reading frame are listed below. Nine of these substitutions did not result in a change in the encoded amino acid), while 3 resulted in conservative substitutions and 3 resulted in nonconservative substitutions.

Apparent polymorphisms in the hedg protein coding region.

| Nucleotide Position & Polymorphism | Affected Codon | Amino Acid Predicted | Consequence |
|---|---|---|---|
| 491 | TTC | Phenylalanine | |
|  | TTT | Phenylalanine | Silent |
| 585 | CTG | Leucine | |
|  | TTG | Leucine | Silent |
| 716 | GTC | Valine | |
|  | GTT | Valine | Silent |
| 779 | ATC | Isoleucine | |
|  | ATT | Isoleucine | Silent |
| 781 | TCT | Serine | Nonconservative |
|  | TTT | Phenylalanine | Substitution |
| 788 | TGC | Cysteine | |
|  | TGT | Cysteine | Silent |
| 790 | TCT | Serine | Nonconservative |
|  | TTT | Phenylalanine | Substitution |
| 830 | TTC | Phenylalanine | |
|  | TTT | Phenylalanine | Silent |
| 874 | GTG | Valine | Conservative |
|  | GCG | Alanine | Substitution |
| 887 | ATC | Isoleucine | |
|  | ATT | Isoleucine | Silent |
| 914 | AAC | Asparagine | Conservative |
|  | AAA | Lysine | Substitution |
| 917 | GTC | Valine | |
|  | GTT | Valine | Silent |
| 922 | TCT | Serine | Nonconservative |
|  | TTT | Phenylalanine | Substitution |
| 1041 | CTC | Leucine | Conservative |
|  | TTC | Phenylalanine | Substitution |
| 1277 | GAG | Glutamate | |
|  | GAA | Glutamate | Silent |

The edg-5 open reading frame of the pC3-hEdg5 (SEQ ID NO:13; FIG. 3) clone predicts a 353 amino acid polypeptide (SEQ ID NO:14; FIG. 4) with many typical features of a GPCR. These include:

1. A hydropathy profile consistent with the 7 transmembrane structure of GPCRs:

N-terminal extracellular domain: 1–30

TM-1: 31–56

IL-1: 57–63

TM-2: 64–92

EL-1: 93–106

TM-3: 107–125

IL-2: 126–144

TM-4: 145–170

EL-2: 171–186

TM-5: 187–207

IL-3: 208–239

TM-6: 240–261

EL-3: 262–276

TM-7: 277–297

C-terminal cytoplasmic domain: 298–353
2. Potential N-glycosylation site in the extracellular N-terminal domain, at residue 15
3. Potential N-myristoylation site at residue 345
4. Potential protein kinase C phosphorylation sites at residues 141, 229 and 303
5. Potential cAMP- and cGMP-dependent kinase phosphorylation sites at residues 217, 233 and 321
6. Potential casein kinase-II phosphorylation site at residue 329

The amino acid sequence of the human edg-5 receptor, SEQ ID NO:14 (FIG. 4), also shows high homology with other members of the edg subfamily of GPCRs. A multiple alignment is shown in FIG. 5. The pairwise percent identity and similarity is presented in Table 2 below:

TABLE 2

Percent Amino Acid Identity and Similarity of Edg Family Sequences to the Human Edg-5 receptor

| Gene | Percent Identity | Percent Similarity |
| --- | --- | --- |
| Edg-1 (Human) | 30.1 | 40.9 |
| Edg-2 (Human) | 48.6 | 59.0 |
| Edg-2 (Bovine) | 55.1 | |
| Edg-3 (Human) | 32.6 | 43.3 |
| H218 (Edg-4 - Rat) | 31.6 | 40.6 |
| Edg-6 (Human) | 46.0 | 55.5 |

Multiple sequence alignment indicates that edg-2 is the closest known relative of edg-5 at the amino acid sequence level, as suggested by the DNA sequence. The edg-5 gene product is also closely related to edg-6, a novel edg gene described in copending application U.S. Ser. No. 08/763, 938. Edg-2, edg-5 and edg-6 appear to form a subfamily distinct from edg-1, edg-3 and edg-4 within the larger edg gene family.

Alternative splicing variants of murine edg-2 have been found, which differ in length within the N-terminal coding region. The longer open reading frame (Genbank, accession no:MMU70622) encodes an 18-amino acid N-terminal extension of the shorter open reading frame (Genbank, accession no:MMU48235), and retains the initiator methionine codon of the shorter product as amino acid 19 of the longer product. Due to the sequence relatedness of edg-2 and edg-5 and the fact that the methionine codon of the shorter edg-2 product aligns closely with the initiation codon of hedg, the edg-5 open frame hedg may encode a similar N-terminal extension to the HEDG peptide of SEQ ID NO:13; FIG. 3. Such an extension will result from splicing of sequences found upstream of the hedg sequences presented herein, and will produce one or more spliced mRNA variants with a N-terminal extensions. Briefly, given the instant disclosure the skilled artisan could discover such splice variants by 5' RACE using a commercially available 5' RACE kit (Life Technologies, Cat No: 18374-041) using the approach detailed in start protocols in Molecular Biology (2nd edition, 15–27). Briefly, first strand cDNA is primed using an antisense oligonucleotide specific for hedg and ideally directed to a sequence about 500 nucleotides from the 5' end of the known hedg sequence; kidney and lung RNA are preferred templates for cDNA synthesis. Thereafter, first strand cDNA is then tailed using terminal transferase, for example, with deoxyguanine residues. PCR amplification is primed using an anchor primer complementary to the polyguanine tail and a nested primer specific to hedg.

Example 3

Antisense Analysis

Knowledge of the correct, complete cDNA sequence of HEDG enables its use as a tool for antisense technology in the investigation of gene function. Oligonucleotides, cDNA or genomic fragments comprising the antisense strand of hedg are used either in vitro or in vivo to inhibit expression of the mRNA. Such technology is now well known in the art, and antisense molecules can be designed at various locations along the nucleotide sequences. By treatment of cells or whole test animals with such antisense sequences, the gene of interest is effectively turned off. Frequently, the function of the gene is ascertained by observing behavior at the intracellular, cellular, tissue or organismal level (e.g., lethality, loss of differentiated function, changes in morphology, etc.).

In addition to using sequences constructed to interrupt transcription of a particular open reading frame, modifications of gene expression is obtained by designing antisense sequences to intron regions, promoter/enhancer elements, or even to trans-acting regulatory genes. Similarly, inhibition is achieved using Hogeboom base-pairing methodology, also known as "triple helix" base pairing.

Example 4

Expression of HEDG

Expression of hedg is accomplished by subcloning the cDNAs into appropriate expression vectors and transfecting the vectors into analogous expression hosts for example *E. Coli*. In a particular case, the vector is engineered such that it contains a promoter for β-galactosidase, upstream of the cloning site, followed by sequence containing the amino-terminal Met and the subsequent 7 residues of β-galactosidase. Immediately following these eight residues is an engineered bacteriophage promoter useful for artificial priming and transcription and for providing a number of unique endonuclease restriction sites for cloning.

Induction of the isolated, transfected bacterial strain with IPTG using standard methods produces a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it is obtained by deletion or insertion of the appropriate number of bases using well known methods including in vitro mutagenesis, digestion with exonuclease III or mung bean nuclease, or the inclusion of an oligonucleotide linker of appropriate length.

The hedg cDNA is shuttled into other vectors known to be useful for expression of protein in specific hosts. Oligonucleotide primers containing cloning sites as well as a segment of DNA (about 25 bases) sufficient to hybridize to stretches at both ends of the target cDNA is synthesized chemically by standard methods. These primers are then used to amplify the desired gene segment by PCR. The resulting gene segment is digested with appropriate restriction enzymes under standard conditions and isolated by gel electrophoresis. Alternately, similar gene segments are produced by digestion of the cDNA with appropriate restriction enzymes. Using appropriate primers, segments of coding sequence from more than one gene are ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector also includes an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts require RNA processing elements such as 3' polyadenylation sequences if such are not part of the cDNA of interest.

Additionally, the vector contains promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, are used in mammalian host cells. Once homogeneous cultures of recombinant cells are obtained through standard culture methods, large quantities of recombinantly produced HEDG are recovered from the conditioned medium and analyzed using chromatographic methods known in the art. For example, HEDG can be expressibly cloned into the expression vector pcDNA3, as exemplified herein. This product can be used to transform, for example, HEK293 or COS by methodology standard in the art. Specifically, for example, using Lipofectamine (Gibco BRL catalog no. 18324-020) mediated gene transfer.

Example 5

Isolation of Recombinant HEDG

HEDG is expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequence such as Factor XA or enterokinase (Invitrogen) between the purification domain and the HEDG sequence is useful to facilitate expression of HEDG.

Example 6

Testing of Chimeric T7Gs

Functional chimeric T7Gs are constructed by combining the extracellular and/or transmembrane ligand-receptive sequences of a new isoform with the transmembrane and/or intracellular segments of a different T7G for test purposes. This concept was demonstrated by Kobilka et al (1988, Science 240:1310–1316) who created a series of chimeric α2-β2 adrenergic receptors (AR) by inserting progressively greater amounts of α2-AR transmembrane sequence into β2-AR. The binding activity of known agonists changed as the molecule shifted from having more α2 than β2 conformation, and intermediate constructs demonstrated mixed specificity. The specificity for binding antagonists, however, correlated with the source of the domain VII. The importance of T7G domain VII for ligand recognition was also found in chimeras utilizing two yeast α-factor receptors and is significant because the yeast receptors are classified as miscellaneous receptors. Thus, functional role of specific domains appears to be preserved throughout the T7G family regardless of category.

In parallel fashion, internal segments or cytoplasmic domains from a particular isoform are exchanged with the analogous domains of a known T7G and used to identify the structural determinants responsible for coupling the receptors to trimeric G-proteins (Dohlman et al (1991) Annu Rev Biochem 60:653–88). A chimeric receptor in which domains V, VI, and the intracellular connecting loop from β2-AR were substituted into a2-AR was shown to bind ligands with a2-AR specificity, but to stimulate adenylate cyclase in the manner of β2-AR. This demonstrates that for adrenergic-type receptors, G-protein recognition is present in domains V and VI and their connecting loop. The opposite situation was predicted and observed for a chimera in which the V–>Vl loop from α1-AR replaced the corresponding domain on β2-AR and the resulting receptor bound ligands with β2-AR specificity and activated G-protein-mediated phosphatidylinositol turnover in the α1-AR manner. Finally, chimeras constructed from muscarinic receptors also demonstrated that V–>VI loop is the major determinant for specificity of G-protein activity (Bolander FF, supra).

Chimeric or modified T7Gs containing substitutions in the extracellular and transmembrane regions have shown that these portions of the receptor determine ligand binding specificity. For example, two Ser residues conserved in domain V of all adrenergic and D catecholamine T7G receptors are necessary for potent agonist activity. These serines are believed to form hydrogen bonds with the catechol moiety of the agonists within the T7G binding site. Similarly, an Asp residue present in domain III of all T7Gs which bind biogenic amines is believed to form an ion pair with the ligand amine group in the T7G binding site.

Functional, cloned T7Gs are expressed in heterologous expression systems and their biological activity assessed (e.g. Marullo et al (1988) Proc Natl Acad Sci 85:7551–55; King et al (1990) Science 250:121–23). One heterologous system introduces genes for a mammalian T7G and a mammalian G-protein into yeast cells. The T7G is shown to have appropriate ligand specificity and affinity and trigger appropriate biological activation—growth arrest and morphological changes—of the yeast cells.

An alternate procedure for testing chimeric receptors is based on the procedure utilizing the $P_{2u}$ purinergic receptor ($P_{2u}$) as published by Erb et al (1993, Proc Natl Acad Sci 90:104411–53). Function is easily tested in cultured K562 human leukemia cells because these cells lack $P_{2u}$ receptors. K562 cells are transfected with expression vectors containing either normal or chimeric $P_{2u}$ and loaded with fura-a, fluorescent probe for Ca++. Activation of properly assembled and functional $P_{2u}$ receptors with extracellular UTP or ATP mobilizes intracellular Ca++ which reacts with fura-a and is measured spectrofluorometrically. As with the T7G receptors above, chimeric genes are created by combining sequences for extracellular receptive segments of any newly discovered T7G polypeptide with the nucleotides for the transmembrane and intracellular segments of the known $P_{2u}$ molecule. Bathing the transfected K562 cells in microwells containing appropriate ligands triggers binding and fluorescent activity defining effectors of the T7G molecule. Once ligand and function are established, the $P_{2u}$ system is useful for defining antagonists or inhibitors which block binding and prevent such fluorescent reactions.

Example 7

Production of HEDG Specific Antibodies

Two approaches are utilized to raise antibodies to HEDG, and each approach is useful for generating either polyclonal or monoclonal antibodies. In one approach, denatured protein from reverse phase HPLC separation is obtained in quantities up to 75 mg. This denatured protein is used to immunize mice or rabbits using standard protocols; about 100 micrograms are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg is sufficient for labeling and screening of several thousand clones.

In the second approach, the amino acid sequence of an appropriate HEDG domain, as deduced from translation of the cDNA, is analyzed to determine regions of high antigenicity. Oligopeptides comprising appropriate hydrophilic regions, as illustrated in FIG. 2, SEQ ID NO:15, are synthesized and used in suitable immunization protocols to raise antibodies. Analysis to select appropriate epitopes is described by Ausubel FM et al (supra). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 43 1A using fmoc-chemistry and coupled to keyhole limpet hemocyanin (KLH; Sigma, St. Louis Mo.) by reaction with M-maleimidobenzoyl-N-hydroxysuccinimide ester (MBS; Ausubel FM et al, supra). If necessary, a cysteine is introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine sewm albumin, reacting with antisera, washing and reacting with labeled (radioactive or fluorescent), affinity purified, specific goat anti-rabbit 1gG.

Hybridomas are prepared and screened using standard techniques. Hybridomas of interest are detected by screening with labeled HEDG to identify those fusions producing the monoclonal antibody with the desired specificity. In a typical protocol, wells of plates (FAST; Becton-Dickinson, Palo Alto Calif.) are coated during incubation with affinity purified, specific rabbit anti-mouse (or suitable antispecies 1 g) antibodies at 10 mg/ml. The coated wells are blocked with 1% BSA, washed and incubated with supematants from hybridomas. After washing the wells are incubated with labeled HEDG at 1 mg/ml. Supernatants with specific antibodies bind more labeled HEDG than is detectable in the background. Then clones producing specific antibodies are expanded and subjected to two cycles of cloning at limiting dilution. Cloned hybridomas are injected into pristane-treated mice to produce ascites, and monoclonal antibody is purified from mouse ascetic fluid by affinity chromatography on Protein A. Monoclonal antibodies with affinities of at least $10^8$ M$^{-1}$, preferably $10^9$ to $10^{10}$ or stronger, are typically made by standard procedures as described in Harlow and Lane (1988) Antibodies: A Laboratory Manual, Cold Spring Harbor Laboratory, Cold Spring Harbor, N.Y.; and in Goding (1986) Monoclonal Antibodies: Principles and Practice, Academic Press, New York City, both incorporated herein by reference.

Example 8

Diagnostic Test Using HEDG Specific Antibodies

Particular HEDG antibodies are useful for investigating signal transduction and the diagnosis of infectious or hereditary conditions which are characterized by differences in the amount or distribution of HEDG or downstream products of an active signaling cascade.

Diagnostic tests for HEDG include methods utilizing antibody and a label to detect HEDG in human body fluids, membranes, cells, tissues or extracts of such. The polypeptides and antibodies of the present invention are used with or without modification. Frequently, the polypeptides and antibodies are labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, chromogenic agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, Incorporated herein by reference.

A variety of protocols for measuring soluble or membrane-bound HEDG, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on HEDG is preferred, but a competitive binding assay may be employed. These assays are described, among other places, in Maddox, D E et al (1983, J Exp. Med. 158:1211f).

Example 9

Purification of Native HEDG Using Specific Antibodies

Native or recombinant HEDG is purified by immunoaffinity chromatography using antibodies specific for HEDG. In general, an immunoaffinity column is constructed by covalently coupling the anti-TRH antibody to an activated chromatographic resin.

Polyclonal immunoglobulins are prepared from immune sera either by precipitation with ammonium sulfate or by purification on immobilized Protein A (Pharmacia LKB Biotechnology, Piscataway N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of HEDG by preparing a fraction from cells containing HEDG in a soluble form. This preparation is derived by solubilization of whole cells or of a subcellular fraction obtained via differential centrifugation (with or without addition of detergent) or by other methods well known in the art. Alternatively, soluble HEDG containing a signal sequence is secreted in useful quantity into the medium in which the cells are grown.

A soluble HEDG-containing preparation is passed over the immunoaffinity column, and the column is washed under conditions that allow the preferential absorbance of HEDG (e.g., high ionic strength buffers in the presence of detergent). Then, the column is eluted under conditions that disrupt antibody/protein binding (e.g., a buffer of pH 2–3 or a high concentration of a chaotrope such as urea or thiocyanate ion), and HEDG is collected.

Example 10

Drug Screening

This invention is particularly useful for screening therapeutic compounds by using HEDG or binding fragments thereof in any of a variety of drug screening techniques. As HEDG is a G protein coupled receptor any of the methods commonly used in the art may potentially used to identify HEDG ligands. For example, the activity of a G protein coupled receptor such as HEDG can be measured using any of a variety of appropriate functional assays in which activation of the receptor results in an observable change in the level of some second messenger system, such as adenylate cyclase, guanylyl cyclase, calcium mobilization, or inositol phospholipid hydrolysis. One such approach, measures the effect of ligand binding on the activation of intracellular second messenger pathways, using a reporter gene. Typically, the reporter gene will have a promoter which is sensitive to the level of that second messenger controlling expression of an easily detectable gene product, for example, CAT or luciferase. Alternatively, the cell is loaded with a reporter substance, e.g., FURA whereby changes in the intracellular concentration of calcium indicate modulation of the receptor as a result of ligand binding. Thus, the present invention provides methods of screening for drugs or any other agents which affect signal transduction.

Alternatively, the polypeptide or fragment employed in such a test is either free in solution, affixed to a solid support, borne on a cell surface or located intracellularly. One method of drug screening utilizes eukaryotic or prokaryotic host cells which are stabley transformed with recombinant nucleic acids expressing the polypeptide or fragment. Drugs are screened against such transformed cells in competitive binding assays. Such cells, either in viable or fixed form, are used for standard binding assays. One measures, for example, the formation of complexes between HEDG and the agent being tested. Alternatively, one examines the diminution in complex formation between HEDG and a ligand caused by the agent being tested.

This invention also contemplates the use of competitive drug screening assays in which neutralizing antibodies capable of binding HEDG specifically compete with a test compound for binding to HEDG polypeptides or fragments thereof. In this manner, the antibodies are used to detect the presence of any peptide which shares one or more antigenic determinants with HEDG.

Example 11

Rational Drug Design

Herein, the goal of rational drug design is to produce structural analogs of biologically active phospholipids of interest or of small molecules with which they interact, agonists, antagonists, or inhibitors. Any of these examples are used to fashion drugs which are more active or stable forms of the phospholipid or which enhance or interfere with the function of a phospholipid in vivo.

In one approach, the three-dimensional structure of a protein of interest, or of a protein-inhibitor complex, is determined by x-ray crystallography, by computer modeling or, most typically, by a combination of the two approaches. Both the shape and charges of the polypeptide must be ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design includes molecules which have improved activity or stability as shown by Braxton S and Wells J A (1992, Biochemistry 31:7796–7801) or which act as inhibitors, agonists, or antagonists of native peptides as shown by Athauda S B et al (1993 J Biochem 113:742–46), incorporated herein by reference.

It is also possible to isolate a target-specific antibody, selected by functional assay, as described above, and then to solve its crystal structure. This approach, in principle, yields a pharmacore upon which subsequent drug design is based. It is possible to bypass protein crystallography altogether by generating anti-idiotypic antibodies (anti-ids) to a functional, pharmacologically active antibody. As a mirror image of a mirror image, the binding site of the anti-ids is expected to be an analog of the original receptor. The anti-id is then used to identify and isolate peptides from banks of chemically or biologically produced peptides. The isolated peptides then act as the pharmacore.

By virtue of the present invention, sufficient amount of polypeptide are made available to perform such analytical studies as X-ray crystallography. In addition, knowledge of the HEDG amino acid sequence provided herein provides guidance to those employing computer modeling techniques in place of or in addition to x-ray crystallography.

Example 12

Use and Administration of Antibodies, Inhibitors, or Antagonists

Antibodies, inhibitors, or antagonists of HEDG (or other treatments to limit signal transduction, LST) provide different effects when administered therapeutically. LSTs are formulated in a nontoxic, inert, pharmaceutically acceptable aqueous carrier medium preferably at a pH of about 5 to 8, more preferably 6 to 8, although pH may vary according to the characteristics of the antibody, inhibitor, or antagonist being formulated and the condition to be treated. Characteristics of LSTs include solubility of the molecule, half-life and antigenicity/immunogenicity. These and other characteristics aid in defining an effective carrier.

LSTs are delivered by known routes of administration including but not limited to topical creams and gels; transmucosal spray and aerosol; transdermal patch and bandage; injectable, intravenous and lavage formulations; and orally administered liquids and pills particularly formulated to resist stomach acid and enzymes. The particular formulation, exact dosage, and route of administration is determined by the attending physician and varies according to each specific situation.

Such determinations are made by considering multiple variables such as the condition to be treated, the LST to be administered, and the pharmacokinetic profile of a particular LST. Additional factors which are taken into account include severity of the disease state, patient's age, weight, gender and diet, time and frequency of LST administration, possible combination with other drugs, reaction sensitivities, and tolerance/response to therapy. Long acting LST formulations might be administered every 3 to 4 days, every week, or once every two weeks depending on half-life and clearance rate of the particular LST.

Normal dosage amounts vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. Those skilled in the art employ different formulations for different LSTs. Administration to cells such as nerve cells necessitates delivery in a manner different from that to other cells such as vascular endothelial cells.

It is contemplated that abnormal signal transduction, trauma, or diseases which trigger HEDG activity are treatable with LSTs. These conditions or diseases are specifically diagnosed by the tests discussed above, and such testing should be performed in suspected cases of viral, bacterial or fungal infections: allergic responses; mechanical injury associated with trauma; hereditary diseases; lymphoma or carcinoma; or other conditions which activate the genes of lymphoid or neuronal tissues.

Example 13

Production of Transgenic Animals

Animal model systems which elucidate the physiological and behavioral roles of the HEDG receptor are produced by creating transgenic animals in which the activity of the HEDG receptor is either increased or decreased, or the amino acid sequence of the expressed HEDG receptor is altered, by a variety of techniques. Examples of these techniques include, but are not limited to: 1) Insertion of normal or mutant versions of DNA encoding a HEDG receptor, by microinjection, electroporation, retroviral transfection or other means well known to those skilled in the art, into appropriate fertilized embryos in order to produce a transgenic animal or 2) Homologous recombination of mutant or normal, human or animal versions of these genes with the native gene locus in transgenic animals to alter the regulation of expression or the structure of these HEDG receptor sequences. The technique of homologous recombination is well known in the art. It replaces the native gene with the inserted gene and so is useful for producing an animal that cannot express native HEDG receptors but does express, for example, an inserted mutant HEDG receptor, which has replaced the native HEDG receptor in the animal's genome by recombination, resulting in underexpression of the transporter. Microinjection adds genes to the genome, but does not remove them, and so is useful for producing an animal which expresses its own and added HEDG receptors, resulting in overexpression of the HEDG receptors.

One means available for producing a transgenic animal, with a mouse as an example, is as follows: Female mice are mated, and the resulting fertilized eggs are dissected out of their oviducts. The eggs are stored in an appropriate medium such as M2 medium. DNA or cDNA encoding a HEDG purified from a vector by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the trans-gene. The DNA, in an appropriately buffered solution, is put into a microinjection needle (which may be made from capillary tubing using a piper puller) and the egg to be injected is put in a depression slide. The needle is inserted into the pronucleus of the egg, and the DNA solution is injected. The injected egg is then transferred into the oviduct of a pseudopregnant mouse (a mouse stimulated by the appropriate hormones to maintain pregnancy but which is not actually pregnant), where it proceeds to the uterus, implants, and develops to term. As noted above, microinjection is not the only methods for inserting DNA into the egg cell, and is used here only for exemplary purposes.

All publications and patents mentioned in the above specification are herein incorporated by reference.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

Example 14

Isolation, Chromosomal Localization and Partial Sequencing of a hedg Genomic Clone To identify genomic clones containing the hedg gene, the H501-20F (SEQ ID NO: 6) and H501-246R (SEQ ID NO: 7) primers were used to amplify human genomic DNA as described in Example 2. One microliter of human genomic DNA (Clontech; Cat #6550-1) was used as template. The PCR product was purified and sequenced in-house, using the PCR primers to prime the sequencing reactions. The sequence of this product matched the cDNA sequence previously obtained for hedg, indicating that these primers could be used to identify genomic clones containing this region of the hedg gene.

An arrayed library of genomic DNA clones (Genome Sciences Inc.) was screened by PCR using these primers. The library contained bacterial artificial chromosome (BAC) constructs with ~120 kb human genomic DNA inserts. In total, clones representing about 3 haploid genome equivalents were screened using the edg-5 diagnostic PCR primers. Two clones were identified by this method: BAC-28 (1F) and BAC-236 (13M). Once the DNA from these clones was received, their identity was verified in-house by sequencing of the PCR product we obtained using the edg-5 diagnostic primers: this analysis showed both clones represent at least part of the hedg gene. The BAC-28 (1F) clone was subsequently used to localize the gene on human chromosomes by fluorescent in situ hybridization (FISH) at Genome Systems Inc. The locus for the hedg gene mapped to band p22.3 of human chromosome 1.

A search of the on-line Mendelian Inheritance in Man database revealed two entries for inherited diseases which genetically map to this region, but for which genes have not yet been cloned. These were the database entries 154280 (Malignant Transformation Suppression-1 or MTS1) and 157900 (Moebius Syndrome). The first represents a dominant suppresser of cellular transformation (a class of genes called tumor suppressers or anti-oncogenes), while the second is an inherited syndrome in which the sixth and seventh cranial nerves are small or absent, leading to facial paralysis. Whether edg-5 gene defects contribute to either of these phenotypes is not known.

Sequencing was performed on DNA prepared from BAC-28 (1 F) to determine the position(s) of introns (if any) within the coding region of the edg-5 gene. Sequencing results showed that only one intron exists within the coding region of hedg, at a position indicated by the arrowhead between nt 996/997 of the sequence shown in FIG. 3. This intron falls within the codon for Gly-246 of the edg-5 amino acid sequence. Additional sequencing was performed in the region flanking the 5' end of the edg-5 cDNA sequence derived from pC3-hEdg5, revealing 250 bp of genomic DNA sequence upstream of the 5' end of the cDNA.

Example 15

Expression and Tissue Distribution of Edg-5 RNA in the Rat.

Northern blotting was carried out with the edg-5 cDNA insert by techniques well-known in the art. Two different multi-tissue rat RNA blots (Origene Cat. MB-1005 and MB-1007) were probed with radiolabeled edg-5 cDNA. Washing was performed at high stringency conditions that do not permit detection of edg-2 or other related transcripts. The blots were then subjected to autoradiography. The Northern blot results show that RNA expression levels are highest in lung, kidney and testis. Lower RNA levels were seen in skin, heart, small intestine and stomach. Little or no detectable RNA was found in thymus, brain, spleen and liver. Muscle tissue may also express low levels of edg-5 mRNA. Further, anti-sense oligonucletide probes based on the hedg sequence disclosed herein can be used by those of skill in the art to for in situ hybridization expression studies.

What is claimed is:

1. An isolated polynucleotide encoding a mammalian edg-5 receptor.

2. The polynucleotide of claim 1 comprising the nucleic acid sequence for (hedg) of SEQ. ID NO:13.

3. An isolated nucleic acid comprising the complement of the polynucleotide of claim 2.

4. A composition comprising the isolated nucleic acid of claim 3 in an acceptable excipient.

5. A composition comprising an oligomer of the polynucleotide of claim 2.

6. An expression vector comprising the polynucleotide of claim 1.

7. A host cell transformed with the expression vector of claim 6.

8. A method for producing a polypeptide, said method comprising the steps of:
    a) culturing the host cell of claim 7 under conditions suitable for the expression of the polypeptide; and
    b) recovering the polypeptide from the host cell culture.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

AAYTRSATMT STAAYYTGCG TGCGA                          25

(2) INFORMATION FOR SEQ ID NO:2:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: Modified Site
      (B) LOCATION:4
      (D) OTHER INFORMATION: N is Inosine (ix) FEATURE:
      (A) NAME/KEY: Modified Site
      (B) LOCATION:13
      (D) OTHER INFORMATION: N is Inosine (ix) FEATURE:
      (A) NAME/KEY: Modified Site (B) LOCATION:16
        (D) OTHER INFORMATION: N is Inosine (ix) FEATURE:
        (A) NAME/KEY: Modified Site
        (B) LOCATION:22
        (D) OTHER INFORMATION: N is Inosine (ix) FEATURE:
        (A) NAME/KEY: Modified Site
        (B) LOCATION:25
        (D) OTHER INFORMATION: N is Inosine (ix) FEATURE:
        (A) NAME/KEY: Modified Site
        (B) LOCATION:28
        (D) OTHER INFORMATION: N is Inosine (xi) SEQUENCE DESCRIPTION: SEQ ID NO:2:

CTGNYKWTTC ATNAWNMMRT ANAYNAYNGG RTT                         33

(2) INFORMATION FOR SEQ ID NO:3:

(i) SEQUENCE CHARACTERISTICS:
        (A) LENGTH: 639 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 1..634

(xi) SEQUENCE DESCRIPTION: SEQ ID NO:3:

```
AAC ACT GGC CCG GTG TCG AAA ACG TTG ACC GTC AAC CGC TGG TTC CTC       48
Asn Thr Gly Pro Val Ser Lys Thr Leu Thr Val Asn Arg Trp Phe Leu
 1               5                  10                  15

CGC CAG GGG CTC CTA GAC ACC AGC CTG ACT GCC TCC CTG GCC AAT TTG       96
Arg Gln Gly Leu Leu Asp Thr Ser Leu Thr Ala Ser Leu Ala Asn Leu
                20                  25                  30

CTG GTT ATT GCT GTG GAA AGA CAC ATG TCN ATC ATG AGG ATG AGA GTC      144
Leu Val Ile Ala Val Glu Arg His Met Ser Ile Met Arg Met Arg Val
            35                  40                  45

CAC AGC AAC TTG ACC AAA AAG CGG GTG ACG CTG CTC ATT CTG CTG GTG      192
His Ser Asn Leu Thr Lys Lys Arg Val Thr Leu Leu Ile Leu Leu Val
        50                  55                  60

TGG GCC ATC GCC ATC TTC ATG GGG GCC GTC CCC ACN CTG GGA TGG AAT      240
Trp Ala Ile Ala Ile Phe Met Gly Ala Val Pro Thr Leu Gly Trp Asn
 65                  70                  75                  80

TGC CTC TGC AAC ATC TCG GCC TGC TCT TCT CTG GCT CCC ATT TAC AGT      288
Cys Leu Cys Asn Ile Ser Ala Cys Ser Ser Leu Ala Pro Ile Tyr Ser
                85                  90                  95

AGG AGT TAC CTC ATT TTC TGG ACT GTG TCC AAC CTC CTG GCC TTC TTC      336
Arg Ser Tyr Leu Ile Phe Trp Thr Val Ser Asn Leu Leu Ala Phe Phe
                100                 105                 110

ATC ATG GTG GCG GTA TAC GTA CGC ATC TAC ATG TAT GTT AAA AGG AAA      384
Ile Met Val Ala Val Tyr Val Arg Ile Tyr Met Tyr Val Lys Arg Lys
            115                 120                 125

ACC AAC GTC TTA TCT CCA CAC ACC AGT GGC TCC ATC AGC CGC GGG AGG      432
Thr Asn Val Leu Ser Pro His Thr Ser Gly Ser Ile Ser Arg Arg Arg
        130                 135                 140

GCT CCC ATG AAG CTA ATG AAG ACA GTG ATG ACC GTC TTA GGC GCC TTC      480
Ala Pro Met Lys Leu Met Lys Thr Val Met Thr Val Leu Gly Ala Phe
145                 150                 155                 160
```

```
GTG GTG TGC TGG ACC CCG GGT CTG GTG GTT CTG CTG CTG GAC GGC CTG          528
Val Val Cys Trp Thr Pro Gly Leu Val Val Leu Leu Leu Asp Gly Leu
                165                 170                 175

AAC TGC AAG CAG TGT AAC GTG CAA CAC GTG AAG NGC TGG TTC CTG CTG          576
Asn Cys Lys Gln Cys Asn Val Gln His Val Lys Xaa Trp Phe Leu Leu
                180                 185                 190

CTC GCA CTG CTC AAC TCC GTC ATG AAC CCC CTC ATC TAC TGC CGC TCT          624
Leu Ala Leu Leu Asn Ser Val Met Asn Pro Leu Ile Tyr Cys Arg Ser
                195                 200                 205

CCN NAC TTT CCA TGG                                                      639
Pro Xaa Phe Pro Trp
        210
```

(2) INFORMATION FOR SEQ ID NO:4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TTTTTACTCG AGATTTGCTG GTTATTGCTG TGGAAAG                                  37

(2) INFORMATION FOR SEQ ID NO:5:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TTTTTTCTAG ACGGTCATCA CTGTCTTCAT TAGCTTC                                  37

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATGCGGCTGC ATAGCAACCT GACCAAAAAG                                          30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATCCGCAGGT ACACCACAAC CATGATGAGG                                          30

(2) INFORMATION FOR SEQ ID NO:8:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:8:

TTTTGAGCAA GTTCAGCCTG GTTAAGT                                27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TGGCTTATGA GTATTTCTTC CAGGGTA                                27

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGGTAGTCGG TACCTCTAGA GCAAGTTCAG CC                          32

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ATAACAGAGG ATCCTCGAGT ATTTCTTCCA G                           31

(2) INFORMATION FOR SEQ ID NO:12:

(i) SEQUENCE CHARACTERISTICS:
        (A) LENGTH: 1523 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 261..1322

(xi) SEQUENCE DESCRIPTION: SEQ ID NO:12:

CACCTTCCTA ACCTGAGCGG CCTAGCCTGG GAAACAAACA ATTAAAATGT GCGCTAAATG    60

CTGTGGTAGG AGGTCAGGGG CTATGTCCTG GACCAAAGGA CATTTGCACT GAGACCTGAC   120

ACTTCAGGTC TTCAACTCCC TTGATGGGAG TTAGCCAGAA CGGGCTTAGA AACAGCAATT   180

```
GATGGCTTAG TGACTGATTT TACAAATGAT ATTTGTTTCT TCTTTAAATT TCTTTCTAGG       240

ATGTTCACTT CTTCTCCACA ATG AAT GAG TGT CAC TAT GAC AAG CAC ATG          290
                     Met Asn Glu Cys His Tyr Asp Lys His Met
                                 215                 220

GAC TTT TTT TAT AAT AGG AGC AAC ACT GAT ACT GTC GAT GAC TGG ACA        338
Asp Phe Phe Tyr Asn Arg Ser Asn Thr Asp Thr Val Asp Asp Trp Thr
            225                 230                 235

GGA ACA AAG CTT GTG ATT GTT TTG TGT GTT GGG ACG TTT TTC TGC CTG        386
Gly Thr Lys Leu Val Ile Val Leu Cys Val Gly Thr Phe Phe Cys Leu
            240                 245                 250

TTT ATT TTT TTT TCT AAT TCT CTG GTC ATC GCG GCA GTG ATC AAA AAC        434
Phe Ile Phe Phe Ser Asn Ser Leu Val Ile Ala Ala Val Ile Lys Asn
            255                 260                 265

AGA AAA TTT CAT TTC CCC TTT TAC TAC CTG TTG GCT AAT TTA GCT GCT        482
Arg Lys Phe His Phe Pro Phe Tyr Tyr Leu Leu Ala Asn Leu Ala Ala
270                 275                 280                 285

GCC GAT TTC TTC GCT GGA ATT GCC TAT GTA TTC CTG ATG TTT AAC ACA        530
Ala Asp Phe Phe Ala Gly Ile Ala Tyr Val Phe Leu Met Phe Asn Thr
                290                 295                 300

GGC CCA GTT TCA AAA ACT TTG ACT GTC AAC CGC TGG TTT CTC CGT CAG        578
Gly Pro Val Ser Lys Thr Leu Thr Val Asn Arg Trp Phe Leu Arg Gln
                305                 310                 315

GGG CTT CTG GAC AGT AGC TTG ACT GCT TCC CTC ACC AAC TTG CTG GTT        626
Gly Leu Leu Asp Ser Ser Leu Thr Ala Ser Leu Thr Asn Leu Leu Val
                320                 325                 330

ATC GCC GTG GAG AGG CAC ATG TCA ATC ATG AGG ATG CGG GTC CAT AGC        674
Ile Ala Val Glu Arg His Met Ser Ile Met Arg Met Arg Val His Ser
                335                 340                 345

AAC CTG ACC AAA AAG AGG GTG ACA CTG CTC ATT TTG CTT GTC TGG GCC        722
Asn Leu Thr Lys Lys Arg Val Thr Leu Leu Ile Leu Leu Val Trp Ala
350                 355                 360                 365

ATC GCC ATT TTT ATG GGG GCG GTC CCC ACA CTG GGC TGG AAT TGC CTC        770
Ile Ala Ile Phe Met Gly Ala Val Pro Thr Leu Gly Trp Asn Cys Leu
                370                 375                 380

TGC AAC ATC TCT GCC TGC TCT TCC CTG GCC CCC ATT TAC AGC AGG AGT        818
Cys Asn Ile Ser Ala Cys Ser Ser Leu Ala Pro Ile Tyr Ser Arg Ser
                385                 390                 395

TAC CTT GTT TTC TGG ACA GTG TCC AAC CTC ATG GCC TTC CTC ATC ATG        866
Tyr Leu Val Phe Trp Thr Val Ser Asn Leu Met Ala Phe Leu Ile Met
                400                 405                 410

GTT GTG GTG TAC CTG CGG ATC TAC GTG TAC GTC AAG AGG AAA ACC AAC        914
Val Val Val Tyr Leu Arg Ile Tyr Val Tyr Val Lys Arg Lys Thr Asn
                415                 420                 425

GTC TTG TCT CCG CAT ACA AGT GGG TCC ATC AGC CGC CGG AGG ACA CCC        962
Val Leu Ser Pro His Thr Ser Gly Ser Ile Ser Arg Arg Arg Thr Pro
430                 435                 440                 445

ATG AAG CTA ATG AAG ACG GTG ATG ACT GTC TTA GGG GCG TTT GTG GTA       1010
Met Lys Leu Met Lys Thr Val Met Thr Val Leu Gly Ala Phe Val Val
                450                 455                 460

TGC TGG ACC CCG GGC CTG GTG GTT CTG CCC CTC GAC GGC CTG AAC TGC       1058
Cys Trp Thr Pro Gly Leu Val Val Leu Pro Leu Asp Gly Leu Asn Cys
                465                 470                 475

AGG CAG TGT GGC GTG CAG CAT GTG AAA AGG TGG TTC CTG CTG CTG GCG       1106
Arg Gln Cys Gly Val Gln His Val Lys Arg Trp Phe Leu Leu Leu Ala
                480                 485                 490

CTG CTC AAC TCC GTC GTG AAC CCC ATC ATC TAC TCC TAC AAG GAC GAG       1154
Leu Leu Asn Ser Val Val Asn Pro Ile Ile Tyr Ser Tyr Lys Asp Glu
                495                 500                 505
```

```
GAC ATG TAT GGC ACC ATG AAG AAG ATG ATC TGC TGC TTC TCT CAG GAG    1202
Asp Met Tyr Gly Thr Met Lys Lys Met Ile Cys Cys Phe Ser Gln Glu
510                 515                 520                 525

AAC CCA GAG AGG CGT CCC TCT CGC ATC CCC TCC ACA GTC CTC AGC AGG    1250
Asn Pro Glu Arg Arg Pro Ser Arg Ile Pro Ser Thr Val Leu Ser Arg
                530                 535                 540

AGT GAC ACA GGC AGC CAG TAC ATA GAG GAT AGT ATT AGC CAA GGT GCA    1298
Ser Asp Thr Gly Ser Gln Tyr Ile Glu Asp Ser Ile Ser Gln Gly Ala
            545                 550                 555

GTC TGC AAT AAA AGC ACT TCC TAA ACTCTGGATG CCTCTYGGCC CACCCAGGCC   1352
Val Cys Asn Lys Ser Thr Ser *
            560                 565

TCCTCTGGGA AAAGAGCTGT TAAGAATGAT TACCTGTCTC TAACAAAGCC CATGTACAGT  1412

GTTATTTGAG GTCTCCATTA ATCACTGCTA GATTTCTTTA AAAAATTTTT TTTCATAGTT  1472

TAAAAGCATG GCAGTAAAG AGAGGACCTG CTGCATTTAG AGAAAGCACA G           1523
```

(2) INFORMATION FOR SEQ ID NO:13:

(i) SEQUENCE CHARACTERISTICS:
        (A) LENGTH: 1356 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
GAATTCGCGG CCGCGTCGAC GTTCACTTCT CCACAATGAA TGAGTGTCAC TATGACAAGC    60

ACATGGACTT TTTTTATAAT AGGAGCAACA CTGATACTGT CGATGACTGG ACAGGAACAA   120

AGCTTGTGAT TGTTTTGTGT GTTGGGACGT TTTTCTGCCT GTTTATTTTT TTTTCTAATT   180

CTCTGGTCAT CGCGGCAGTG ATCAAAAACA GAAAATTTCA TTTCCCCTTT TACTACCTGT   240

TGGCTAATTT AGCTGCTGCC GATTTCTTCG CTGGAATTGC CTATGTATTC CTGATGTTTA   300

ACACAGGCCC AGTTTCAAAA ACTTTGACTG TCAACCGCTG GTTTCTCCGT CAGGGGCTTC   360

TGGACAGTAG CTTGACTGCT TCCCTCACCA ACTTGCTGGT TATCGCCGTG GAGAGGCACA   420

TGTCAATCAT GAGGATGCGG GTCCATAGCA ACCTGACCAA AAAGAGGGTG ACACTGCTCA   480

TTTTGCTTGT CTGGGCCATC GCCATTTTTA TGGGGGCGGT CCCCACACTG GCTGGAATT    540

GCCTCTGCAA CATCTCTGCC TGCTCTTCCC TGGCCCCCAT TTACAGCAGG AGTTACCTTG   600

TTTTCTGGAC AGTGTCCAAC CTCATGGCCT TCCTCATCAT GGTTGTGGTG TACCTGCGGA   660

TCTACGTGTA CGTCAAGAGG AAAACCAACG TCTTGTCTCC GCATACAAGT GGGTCCATCA   720

GCCGCCGGAG GACACCCATG AAGCTAATGA AGACGGTGAT GACTGTCTTA GGGGCGTTTG   780

TGGTATGCTG GACCCCGGGC CTGGTGGTTC TGCCCCTCGA CGGCCTGAAC TGCAGGCAGT   840

GTGGCGTGCA GCATGTGAAA AGGTGGTTCC TGCTGCTGGC GCTGCTCAAC TCCGTCGTGA   900

ACCCCATCAT CTACTCCTAC AAGGACGAGG ACATGTATGG CACCATGAAG AAGATGATCT   960

GCTGCTTCTC TCAGGAGAAC CCAGAGAGGC GTCCCTCTCG CATCCCCTCC ACAGTCCTCA  1020

GCAGGAGTGA CACAGGCAGC CAGTACATAG AGGATAGTAT TAGCCAAGGT GCAGTCTGCA  1080

ATAAAAGCAC TTCCTAAACT CTGGATGCCT CTGGCCCACC CAGGCCTCCT CTGGGAAAAG  1140

AGCTGTTAAG AATGATTACC TGTCTCTAAC AAAGCCCATG TACAGTGTTA TTTGAGGTCT  1200

CCATTAATCA CTGCTAGATT TCTTTAAAAA ATTTTTTTTC ATAGTTTAAA AGCATGGGCA  1260

GTAAAGAGAG GACCTGCTGC ATTTAGAGAA AGCACAGGTC GACGCGGCCG CGAATTCTTT  1320
```

TGCTTTTTAC CCTGGAAGAA ATACTCGAGC ATGCAT 1356

(2) INFORMATION FOR SEQ ID NO:14:

(i) SEQUENCE CHARACTERISTICS:
      (A) LENGTH: 353 amino acids
      (B) TYPE: amino acid
      (D) TOPOLOGY: linear (ii) MOLECULE TYPE: protein (xi) SEQUENCE DESCRIPTION: SEQ ID NO:14:

```
Met Asn Glu Cys His Tyr Asp Lys His Met Asp Phe Phe Tyr Asn Arg
  1               5                  10                  15

Ser Asn Thr Asp Thr Val Asp Asp Trp Thr Gly Thr Lys Leu Val Ile
                 20                  25                  30

Val Leu Cys Val Gly Thr Phe Phe Cys Leu Phe Ile Phe Phe Ser Asn
             35                  40                  45

Ser Leu Val Ile Ala Ala Val Ile Lys Asn Arg Lys Phe His Phe Pro
         50                  55                  60

Phe Tyr Tyr Leu Leu Ala Asn Leu Ala Ala Ala Asp Phe Phe Ala Gly
 65                  70                  75                  80

Ile Ala Tyr Val Phe Leu Met Phe Asn Thr Gly Pro Val Ser Lys Thr
                 85                  90                  95

Leu Thr Val Asn Arg Trp Phe Leu Arg Gln Gly Leu Leu Asp Ser Ser
                100                 105                 110

Leu Thr Ala Ser Leu Thr Asn Leu Leu Val Ile Ala Val Glu Arg His
            115                 120                 125

Met Ser Ile Met Arg Met Arg Val His Ser Asn Leu Thr Lys Lys Arg
        130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175

Ser Ser Leu Ala Pro Ile Tyr Ser Arg Ser Tyr Leu Val Phe Trp Thr
            180                 185                 190

Val Ser Asn Leu Met Ala Phe Leu Ile Met Val Val Tyr Leu Arg
        195                 200                 205

Ile Tyr Val Tyr Val Lys Arg Lys Thr Asn Val Leu Ser Pro His Thr
    210                 215                 220

Ser Gly Ser Ile Ser Arg Arg Arg Thr Pro Met Lys Leu Met Lys Thr
225                 230                 235                 240

Val Met Thr Val Leu Gly Ala Phe Val Val Cys Trp Thr Pro Gly Leu
                245                 250                 255

Val Val Leu Pro Leu Asp Gly Leu Asn Cys Arg Gln Cys Gly Val Gln
            260                 265                 270

His Val Lys Arg Trp Phe Leu Leu Leu Ala Leu Leu Asn Ser Val Val
        275                 280                 285

Asn Pro Ile Ile Tyr Ser Tyr Lys Asp Glu Asp Met Tyr Gly Thr Met
    290                 295                 300

Lys Lys Met Ile Cys Cys Phe Ser Gln Glu Asn Pro Glu Arg Arg Pro
305                 310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
            340                 345                 350
```

Ser (2) INFORMATION FOR SEQ ID NO:15:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO:15:

```
Asn Thr Gly Pro Val Ser Lys Thr Leu Thr Val Asn Arg Trp Phe Leu
 1               5                  10                  15

Arg Gln Gly Leu Leu Asp Thr Ser Leu Thr Ala Ser Leu Ala Asn Leu
            20                  25                  30

Leu Val Ile Ala Val Glu Arg His Met Ser Ile Met Arg Met Arg Val
        35                  40                  45

His Ser Asn Leu Thr Lys Lys Arg Val Thr Leu Leu Ile Leu Leu Val
    50                  55                  60

Trp Ala Ile Ala Ile Phe Met Gly Ala Val Pro Thr Leu Gly Trp Asn
65                  70                  75                  80

Cys Leu Cys Asn Ile Ser Ala Cys Ser Ser Leu Ala Pro Ile Tyr Ser
                85                  90                  95

Arg Ser Tyr Leu Ile Phe Trp Thr Val Ser Asn Leu Leu Ala Phe Phe
            100                 105                 110

Ile Met Val Ala Val Tyr Val Arg Ile Tyr Met Tyr Val Lys Arg Lys
            115                 120                 125

Thr Asn Val Leu Ser Pro His Thr Ser Gly Ser Ile Ser Arg Arg Arg
    130                 135                 140

Ala Pro Met Lys Leu Met Lys Thr Val Met Thr Val Leu Gly Ala Phe
145                 150                 155                 160

Val Val Cys Trp Thr Pro Gly Leu Val Val Leu Leu Leu Asp Gly Leu
                165                 170                 175

Asn Cys Lys Gln Cys Asn Val Gln His Val Lys Xaa Trp Phe Leu Leu
            180                 185                 190

Leu Ala Leu Leu Asn Ser Val Met Asn Pro Leu Ile Tyr Cys Arg Ser
            195                 200                 205

Pro Xaa Phe Pro Trp
    210
```